US012171979B2

(12) United States Patent
Volkar et al.

(10) Patent No.: US 12,171,979 B2
(45) Date of Patent: Dec. 24, 2024

(54) PRELOADING OF CONTRAST INJECTION PROTOCOLS INTO THE ADMINISTRATION LINE

(71) Applicant: BAYER HEALTHCARE LLC, Whippany, NJ (US)

(72) Inventors: John Volkar, Valencia, PA (US); Corey Kemper, Pittsburgh, PA (US); Barry Iddon, Jeannette, PA (US); James Hoon Yoo, Baulkham Hills (AU); Michael Brooks, Croydon Park (AU)

(73) Assignee: BAYER HEALTHCARE LLC, Whippany, NJ (US)

( * ) Notice: Subject to any disclaimer, the term of this patent is extended or adjusted under 35 U.S.C. 154(b) by 919 days.

(21) Appl. No.: 17/043,802

(22) PCT Filed: Apr. 9, 2019

(86) PCT No.: PCT/US2019/026481
§ 371 (c)(1),
(2) Date: Sep. 30, 2020

(87) PCT Pub. No.: WO2019/199746
PCT Pub. Date: Oct. 17, 2019

(65) Prior Publication Data
US 2021/0015995 A1    Jan. 21, 2021

Related U.S. Application Data

(60) Provisional application No. 62/655,368, filed on Apr. 10, 2018.

(51) Int. Cl.
*A61M 5/00* (2006.01)
*A61B 6/00* (2024.01)
(Continued)

(52) U.S. Cl.
CPC ............. *A61M 5/007* (2013.01); *A61B 6/481* (2013.01); *A61M 5/16827* (2013.01);
(Continued)

(58) Field of Classification Search
CPC .. A61M 5/007; A61M 5/16827; A61M 5/178; A61M 2005/1402; A61M 2005/1403; A61B 6/481
See application file for complete search history.

(56) References Cited

U.S. PATENT DOCUMENTS 7,925,330 B2   4/2011   Kalafut et al.
8,295,914 B2   10/2012  Kalafut et al.
(Continued)

FOREIGN PATENT DOCUMENTS

JP    4417621 B2    2/2010
WO    02096487 A1   12/2002
(Continued)

OTHER PUBLICATIONS

Bayer., "MRXperion OpManual—3038591 Rev H Feb. 13, 2018", Feb. 13, 2018.
(Continued)

*Primary Examiner* — Jason M Ip
(74) *Attorney, Agent, or Firm* — James R. Stevenson; Bojan Popovic

(57) ABSTRACT

A fluid injector system includes a control device operably associated with at least one drive component for use in actuating a plurality of fluid containers in fluid communication with a patient through an administration line. The control device includes at least one processor programmed or configured to enable programming of a diagnostic injection protocol comprising one or more phases according to which at least one of the first and the second fluid containers are selectively actuatable by the at least one drive compo-
(Continued)

nent to enable injection of at least one of a first fluid and a second fluid into the patient. The control device is further programmed or configured to enable selection and commencement of at least partial preloading into the administration line of at least one of the first fluid and the second fluid in accordance with the one or more phases of the diagnostic injection protocol.

18 Claims, 11 Drawing Sheets

(51) Int. Cl.
    *A61M 5/14*         (2006.01)
    *A61M 5/168*       (2006.01)
    *A61M 5/178*       (2006.01)

(52) U.S. Cl.
    CPC ..... *A61M 5/178* (2013.01); *A61M 2005/1402* (2013.01); *A61M 2005/1403* (2013.01); *A61M 2205/502* (2013.01)

(56) References Cited

U.S. PATENT DOCUMENTS

| | | | |
|---|---|---|---|
| 9,008,759 B2 | 4/2015 | Kalafut et al. | |
| 9,302,044 B2 | 4/2016 | Kalafut et al. | |
| 9,421,330 B2 | 8/2016 | Kalafut et al. | |
| 9,750,953 B2 | 9/2017 | Kalafut | |
| 9,949,704 B2 | 4/2018 | Kalafut et al. | |
| 9,959,389 B2 | 5/2018 | Kalafut | |
| 2010/0030073 A1 | 2/2010 | Kalafut et al. | |
| 2014/0224829 A1* | 8/2014 | Capone | B05B 11/1015 222/23 |
| 2015/0127376 A1* | 5/2015 | Ortenzi | A61M 5/14546 705/3 |
| 2016/0331951 A1 | 11/2016 | Sokolov et al. | |
| 2017/0258982 A1 | 9/2017 | Kemper | |
| 2019/0247576 A1* | 8/2019 | Okiyama | A61M 5/1689 |

FOREIGN PATENT DOCUMENTS

| | | |
|---|---|---|
| WO | 2016112163 A1 | 7/2016 |
| WO | 2016152841 A1 | 9/2016 |

OTHER PUBLICATIONS

"Mark 7 Arterion Injection System Operation Manual, Rev. Q", Jan. 21, 2017.

"International Preliminary Report on Patentability from PCT Application PCT/US2019/026481", Oct. 22, 2020.

* cited by examiner

PRELOADING OF CONTRAST INJECTION PROTOCOLS INTO THE ADMINISTRATION LINE

CROSS-REFERENCE TO RELATED APPLICATIONS

This application is a § 371 U.S. national phase application of PCT International Application No. PCT/US2019/026481, filed Apr. 9, 2019, and claims the benefit of U.S. Provisional Patent Application No. 62/655,368, filed Apr. 10, 2018, the disclosures of which are hereby incorporated by reference in their entirety.

BACKGROUND OF THE DISCLOSURE

Field of the Disclosure

The present disclosure relates to a fluid injector system having a control device for enabling at least a partial preloading into an administration line of at least one of a first fluid and a second fluid in accordance with one or more phases of a diagnostic injection protocol. The present disclosure also relates to a computer program product and a computer-implemented method of enabling at least a partial preloading into the administration line of the first and/or second fluids in accordance with one or more phases of a diagnostic injection protocol of the type capable of being carried out by such a fluid injector system.

Description of the Related Art

In many medical diagnostic and therapeutic procedures, a medical practitioner, such as a physician, injects a patient with one or more medical fluids. In recent years, a number of medical fluid delivery systems for pressurized injection of fluids, such as a contrast solution (often referred to simply as "contrast"), a flushing agent, such as saline, and other medical fluids, have been developed for use in procedures such as angiography, computed tomography (CT), ultrasound, magnetic resonance imaging (MRI), positron emission tomography (PET), and other molecular imaging procedures. In general, these medical fluid delivery systems are designed to deliver a preset amount of fluid at a preset flow rate.

A medical fluid delivery system is generally connected to the patient via an administration line. The administration line, however, must be primed with fluid to remove or flush air from the administration line before being attached to the patient to remove air from the administration line. Once the air is removed, the fluid remains in the administration line and is ready to be injected into the patient during the initial stage of the injection procedure. Medical fluid delivery systems are generally calibrated to account for the fluid volume of the administration line and thereby ensure that the proper amount of medical fluid is injected into the patient despite the initial volume of the fluid used to prime the line. However, the relatively large diameter and length of some administration lines results may result in a significant amount of extra fluid being injected into the patient. Particularly if the patient is a child, the volume of the fluid used to prime the administration line may represent a clinically significant amount of fluid relative to the patient's body size and blood volume. Certain adult patients may also be particularly sensitive to the injection of extra fluid for a variety of clinical reasons. Additionally, the volume of the fluid used for priming the administration line may represent a significant amount of the total fluid delivered. Particularly, in MIll procedures, where the total volume of contrast solution may be as low as 2 to 5 milliliters (ml), a typical administration line volume of 8 ml may result in the injection of well over twice the amount of flushing/priming fluid as contrast solution.

SUMMARY OF THE DISCLOSURE

In view of the foregoing, there exists a need for methods of operating medical fluid delivery systems without delivering unnecessary fluids to a patient.

The present disclosure is generally directed to systems, methods, and computer program products for enabling at least partial preloading into an administration line of a fluid injector system in accordance with one or more phases of a diagnostic injection protocol.

In accordance with some aspects and examples of the present disclosure, fluid injector system may include a control device operably associated with at least one drive component for use in actuating a plurality of fluid containers. The plurality of fluid containers may be capable of being placed in fluid communication with a patient through an administration line with a first of the fluid containers capable of being filled with a first fluid including a contrast solution and a second of the fluid containers capable of being filled with a second fluid including a flushing agent. The control device may include at least one processor programmed or configured to enable programming of a diagnostic injection protocol comprising one or more phases according to which at least one of the first and the second fluid containers are selectively actuatable by the at least one drive component to enable injection of at least one of the first fluid and the second fluid via the administration line into the patient so as to effect enhancement of at least one region of interest thereof over a scan duration of a diagnostic imaging procedure. The control device may be further programmed or configured to, upon completion of the programming of the diagnostic injection protocol and priming of the administration line with the second fluid, enable selection and commencement of at least partial preloading into the administration line of at least one of the first fluid and the second fluid in accordance with the one or more phases of the diagnostic injection protocol.

In accordance with some aspects and examples of the present disclosure, the fluid injector system may further include a user interface operably associated with the at least one processor. The user interface may be configured to accept a plurality of user inputs associated with control of a plurality of operations of the fluid injector system. A set of the plurality of user inputs may be associated with the control of a corresponding set of the plurality of operations involved with the enabling of the selection and the commencement of the at least partial preloading into the administration line of the at least one of the first fluid and the second fluid in accordance with the one or more phases of the diagnostic injection protocol.

In accordance with some aspects and examples of the present disclosure, the set of the plurality of user inputs may include: a select preloading command upon entry of which into the user interface the control device readies the fluid injector system for the at least partial preloading of the diagnostic injection protocol into the administration line; a commence preloading command upon entry of which into the user interface after the select preloading command the control device actuates the plurality of fluid containers and thereby commences the at least partial preloading into the administration line of at least one of the first fluid and the second fluid in accordance with the one or more phases of the diagnostic injection protocol; and a disable preloading command upon entry of which into the user interface after the select preloading command the control device disables an effect of the select preloading command.

In accordance with some aspects and examples of the present disclosure, the control device may be further programmed or configured to calculate a total volume of the at least one of the first fluid and the second fluid to be injected according to the diagnostic injection protocol. As such, upon entry of the commence preloading command into the user interface, the control device, upon determining that the total volume of the at least one of the first fluid and the second fluid to be injected according to the diagnostic injection protocol is equal to the capacity of the administration line, actuates one or more of the plurality of fluid containers and thereby preloads into the administration line the total volume of the diagnostic injection protocol in accordance with the one or more phases thereof and thereby expels from the administration line a volume of the second fluid used in the priming of the administration line therewith. The control device, upon determining that the total volume of the at least one of the first fluid and the second fluid to be injected according to the diagnostic injection protocol is less than the capacity of the administration line, actuates one or more of the plurality of fluid containers and thereby preloads into the administration line the total volume of the diagnostic injection protocol in accordance with the one or more phases thereof followed by a supplemental volume of the second fluid equal to the capacity of the administration line minus the total volume of the diagnostic injection protocol and thereby expels from the administration line the volume of the second fluid used in the priming of the administration line therewith. The control device, upon determining that the total volume of the at least one of the first fluid and the second fluid to be injected according to the diagnostic injection protocol is greater than the capacity of the administration line, actuates one or more of the plurality of fluid containers and thereby preloads into the administration line as much of the at least one of the first fluid and the second fluid in accordance with the one or more phases of the diagnostic injection protocol as a capacity of the administration line will allow and retains within the programming a remaining portion of the diagnostic injection protocol until the diagnostic injection protocol is performed on the patient and thereby expels from the administration line the volume of the second fluid used in the priming of the administration line therewith.

In accordance with some aspects and examples of the present disclosure, the user interface may be configured to display information associated with a status of the at least partial preloading into the administration line of at least one of the first fluid and the second fluid in accordance with the one or more phases of the diagnostic injection protocol.

In accordance with some aspects and examples of the present disclosure, the user interface may be configured to display at least one of a total volume of the at least one of the first fluid and the second fluid to be injected according to the diagnostic injection protocol, and for each of the one or more phases of the diagnostic injection protocol, a particular volume of the at least one of the first fluid and the second fluid therein and a flow rate at which the particular volume is to be injected into the patient during administration thereof.

In accordance with some aspects and examples of the present disclosure, the first of the fluid containers may include a syringe and the second of the fluid containers may include a syringe.

In accordance with some aspects and examples of the present disclosure, a computer program product is disclosed for enabling at least partial preloading into an administration line of at least one of a first fluid and a second fluid in accordance with a one or more phases of a diagnostic injection protocol. The computer program product may include at least one non-transitory computer-readable medium including one or more instructions that, when executed by at least one processor, cause the at least one processor to enable programming of the diagnostic injection protocol into a control device of a fluid injector system. The control device may be operably associated with at least one drive component for use in selectively actuating a plurality of fluid containers. The plurality of fluid containers may be capable of being placed in fluid communication with a patient through the administration line with a first of the fluid containers capable of being filled with the first fluid including a contrast solution and a second of the fluid containers capable of being filled with the second fluid including a flushing agent. The one or more instructions, when executed by at least one processor, may further cause the at least one processor to, upon completion of the programming of the diagnostic injection protocol and priming of the administration line with the second fluid, enable selection and commencement of at least partial preloading into the administration line of at least one of the first fluid and the second fluid in accordance with the one or more phases of the diagnostic injection protocol.

In accordance with some aspects and examples of the present disclosure, the one or more instructions, when executed by at least one processor, may further cause the at least one processor to receive, from a user interface operably associated with the at least one processor, at least one of a plurality of user inputs associated with control of a plurality of operations of the fluid injector system. A set of the plurality of user inputs may be associated with the control of a corresponding set of the plurality of operations involved with the enabling of the selection and the commencement of the at least partial preloading into the administration line of the at least one of the first fluid and the second fluid in accordance with the one or more phases of the diagnostic injection protocol.

In accordance with some aspects and examples of the present disclosure, the set of the plurality of user inputs includes: a select preloading command upon entry of which into the user interface the control device readies the fluid injector system for the at least partial preloading of the diagnostic injection protocol into the administration line; a commence preloading command upon entry of which into the user interface after the select preloading command the control device actuates the plurality of fluid containers and thereby commences the at least partial preloading into the administration line of at least one of the first fluid and the second fluid in accordance with the one or more phases of the diagnostic injection protocol; and a disable preloading command upon entry of which into the user interface after the select preloading command the control device disables an effect of the select preloading command.

In accordance with some aspects and examples of the present disclosure, the one or more instructions, when executed by at least one processor, may further cause the at least one processor to calculate a total volume of the at least one of the first fluid and the second fluid to be injected according to the diagnostic injection protocol. As such, upon entry of the commence preloading command into the user interface, the at least one processor, upon determining that the total volume of the at least one of the first fluid and the second fluid to be injected according to the diagnostic injection protocol is equal to the capacity of the administration line, actuates one or more of the plurality of fluid containers and thereby preloads into the administration line the total volume of the diagnostic injection protocol in accordance with the one or more phases thereof and thereby expels from the administration line a volume of the second fluid used in the priming of the administration line therewith. The at least one processor, upon determining that the total volume of the at least one of the first fluid and the second fluid to be injected according to the diagnostic injection protocol is less than the capacity of the administration line, actuates one or more of the plurality of fluid containers and thereby preloads into the administration line the total volume of the diagnostic injection protocol in accordance with the one or more phases thereof followed by a supplemental volume of the second fluid equal to the capacity of the administration line minus the total volume of the diagnostic injection protocol and thereby expels from the administration line the volume of the second fluid used in the priming of the administration line therewith. The at least one processor, upon determining that the total volume of the at least one of the first fluid and the second fluid to be injected according to the diagnostic injection protocol is greater than the capacity of the administration line, actuates one or more of the plurality of fluid containers and thereby preloads into the administration line as much of the at least one of the first fluid and the second fluid in accordance with the one or more phases of the diagnostic injection protocol as a capacity of the administration line will allow and retains within the programming a remaining portion of the diagnostic injection protocol until the diagnostic injection protocol is performed on the patient and thereby expels from the administration line the volume of the second fluid used in the priming of the administration line therewith.

In accordance with some aspects and examples of the present disclosure, the one or more instructions, when executed by at least one processor, may further cause the at least one processor to display, via the user interface, information associated with a status of the at least partial preloading into the administration line of at least one of the first fluid and the second fluid in accordance with the one or more phases of the diagnostic injection protocol.

In accordance with some aspects and examples of the present disclosure, the one or more instructions, when executed by at least one processor, may further cause the at least one processor to display, via the user interface, at least one of a total volume of the at least one of the first fluid and the second fluid to be injected according to the diagnostic injection protocol, and for each of the one or more phases of the diagnostic injection protocol, a particular volume of the at least one of the first fluid and the second fluid therein and a flow rate at which the particular volume is to be injected into the patient during administration thereof.

In accordance with some aspects and examples of the present disclosure, the first of the fluid containers may include a syringe and the second of the fluid containers may include a syringe.

In accordance with some aspects and examples of the present disclosure, a computer-implemented method is disclosed for enabling at least partial preloading into an administration line of at least one of a first fluid and a second fluid in accordance with a one or more phases of a diagnostic injection protocol. The method includes programming, via at least one processor, the diagnostic injection protocol into a control device of a fluid injector system, the control device operably associated with at least one drive component for use in selectively actuating a plurality of fluid containers. The plurality of fluid containers may be capable of being placed in fluid communication with a patient through an administration line with a first of the fluid containers capable of being filled with the first fluid including a contrast solution and a second of the fluid containers capable of being filled with the second fluid including a flushing agent. The method further includes, upon completion of the programming of the diagnostic injection protocol and priming of the administration line with the second fluid, enabling, via the at least one processor, selection and commencement of at least partial preloading into the administration line of at least one of the first fluid and the second fluid in accordance with the one or more phases of the diagnostic injection protocol.

In accordance with some aspects and examples of the present disclosure, the method may further include receiving, from a user interface operably associated with the at least one processor, at least one of a plurality of user inputs associated with control of a plurality of operations of the fluid injector system. A set of the plurality of user inputs may be associated with the control of a corresponding set of the plurality of operations involved with the enabling of the selection and the commencement of the at least partial preloading into the administration line of the at least one of the first fluid and the second fluid in accordance with the one or more phases of the diagnostic injection protocol.

In accordance with some aspects and examples of the present disclosure, the set of the plurality of user inputs may include: a select preloading command upon entry of which into the user interface the control device readies the fluid injector system for the at least partial preloading of the diagnostic injection protocol into the administration line; a commence preloading command upon entry of which into the user interface after the select preloading command the control device actuates the plurality of fluid containers and thereby commences the at least partial preloading into the administration line of at least one of the first fluid and the second fluid in accordance with the one or more phases of the diagnostic injection protocol; and a disable preloading command upon entry of which into the user interface after the select preloading command the control device disables an effect of the select preloading command.

In accordance with some aspects and examples of the present disclosure, the method may further include calculating, with the at least one processor, a total volume of the at least one of the first fluid and the second fluid to be injected according to the diagnostic injection protocol. As such, upon entry of the commence preloading command into the user interface, the control device, upon determining, with the at least one processor, that the total volume of the at least one of the first fluid and the second fluid to be injected according to the diagnostic injection protocol is equal to the capacity of the administration line, actuates one or more of the plurality of fluid containers and thereby preloads into the administration line the total volume of the diagnostic injection protocol in accordance with the one or more phases thereof and thereby expels from the administration line a volume of the second fluid used in the priming of the administration line therewith. The control device, upon determining, with the at least one processor, that the total volume of the at least one of the first fluid and the second fluid to be injected according to the diagnostic injection protocol is less than the capacity of the administration line, actuates one or more of the plurality of fluid containers and thereby preloads into the administration line the total volume of the diagnostic injection protocol in accordance with the one or more phases thereof followed by a supplemental volume of the second fluid equal to the capacity of the administration line minus the total volume of the diagnostic injection protocol and thereby expels from the administration line the volume of the second fluid used in the priming of the administration line therewith. The control device, upon determining, with the at least one processor, that the total volume of the at least one of the first fluid and the second fluid to be injected according to the diagnostic injection protocol is greater than the capacity of the administration line, actuates one or more of the plurality of fluid containers and thereby preloads into the administration line as much of the at least one of the first fluid and the second fluid in accordance with the one or more phases of the diagnostic injection protocol as a capacity of the administration line will allow and retains within the programming a remaining portion of the diagnostic injection protocol until the diagnostic injection protocol is performed on the patient and thereby expels from the administration line the volume of the second fluid used in the priming of the administration line therewith.

In accordance with some aspects and examples of the present disclosure, the method may further include displaying, with the user interface, information associated with a status of the at least partial preloading into the administration line of at least one of the first fluid and the second fluid in accordance with the one or more phases of the diagnostic injection protocol.

In accordance with some aspects and examples of the present disclosure, the method may further include displaying, with the user interface, at least one of: a total volume of the at least one of the first fluid and the second fluid to be injected according to the diagnostic injection protocol; and for each of the one or more phases of the diagnostic injection protocol, a particular volume of the at least one of the first fluid and the second fluid therein and a flow rate at which the particular volume is to be injected into the patient during administration thereof.

In accordance with some aspects and examples of the present disclosure, the first of the fluid containers may include a syringe and the second of the fluid containers may include a syringe.

Further examples of the present disclosure are described in the following non-limiting clauses:

Clause 1. A fluid injector system comprising: a control device operably associated with at least one drive component for use in actuating a plurality of fluid containers, the plurality of fluid containers capable of being placed in fluid communication with a patient through an administration line with a first of the fluid containers capable of being filled with a first fluid comprising a contrast solution and a second of the fluid containers capable of being filled with a second fluid comprising a flushing agent; and the control device including at least one processor programmed or configured to enable programming of a diagnostic injection protocol comprising one or more phases according to which at least one of the first and the second fluid containers are selectively actuatable by the at least one drive component to enable injection of at least one of the first fluid and the second fluid via the administration line into the patient so as to effect enhancement of at least one region of interest thereof over a scan duration of a diagnostic imaging procedure; wherein the control device is further programmed or configured to, upon completion of the programming of the diagnostic injection protocol and priming of the administration line with the second fluid, enable selection and commencement of at least partial preloading into the administration line of at least one of the first fluid and the second fluid in accordance with the one or more phases of the diagnostic injection protocol.

Clause 2. The fluid injector system of clause 1, further including a user interface operably associated with the at least one processor, the user interface being configured to accept a plurality of user inputs associated with control of a plurality of operations of the fluid injector system, wherein a set of the plurality of user inputs is associated with the control of a corresponding set of the plurality of operations involved with the enabling of the selection and the commencement of the at least partial preloading into the administration line of the at least one of the first fluid and the second fluid in accordance with the one or more phases of the diagnostic injection protocol.

Clause 3. The fluid injector system of clause 1 or 2, wherein the set of the plurality of user inputs includes: a select preloading command upon entry of which into the user interface the control device readies the fluid injector system for the at least partial preloading of the diagnostic injection protocol into the administration line; a commence preloading command upon entry of which into the user interface after the select preloading command the control device actuates the plurality of fluid containers and thereby commences the at least partial preloading into the administration line of at least one of the first fluid and the second fluid in accordance with the one or more phases of the diagnostic injection protocol; and a disable preloading command upon entry of which into the user interface after the select preloading command the control device disables an effect of the select preloading command.

Clause 4. The fluid injector system of any of clauses 1-3, wherein the control device is further programmed or configured to calculate a total volume of the at least one of the first fluid and the second fluid to be injected according to the diagnostic injection protocol such that, upon entry of the commence preloading command into the user interface, the control device: upon determining that the total volume of the at least one of the first fluid and the second fluid to be injected according to the diagnostic injection protocol is equal to the capacity of the administration line, actuates one or more of the plurality of fluid containers and thereby preloads into the administration line the total volume of the diagnostic injection protocol in accordance with the one or more phases thereof and thereby expels from the administration line a volume of the second fluid used in the priming of the administration line therewith; upon determining that the total volume of the at least one of the first fluid and the second fluid to be injected according to the diagnostic injection protocol is less than the capacity of the administration line, actuates one or more of the plurality of fluid containers and thereby preloads into the administration line the total volume of the diagnostic injection protocol in accordance with the one or more phases thereof followed by a supplemental volume of the second fluid equal to the capacity of the administration line minus the total volume of the diagnostic injection protocol and thereby expels from the administration line the volume of the second fluid used in the priming of the administration line therewith; and upon determining that the total volume of the at least one of the first fluid and the second fluid to be injected according to the diagnostic injection protocol is greater than the capacity of the administration line, actuates one or more of the plurality of fluid containers and thereby preloads into the administration line as much of the at least one of the first fluid and the second fluid in accordance with the one or more phases of the diagnostic injection protocol as a capacity of the administration line will allow and retains within the programming a remaining portion of the diagnostic injection protocol until the diagnostic injection protocol is performed on the patient and thereby expels from the administration line the volume of the second fluid used in the priming of the administration line therewith.

Clause 5. The fluid injector system of any of clauses 1-4, wherein the user interface is configured to display information associated with a status of the at least partial preloading into the administration line of at least one of the first fluid and the second fluid in accordance with the one or more phases of the diagnostic injection protocol.

Clause 6. The fluid injector system of any of clauses 1-5, wherein the user interface is configured to display at least one of: a total volume of the at least one of the first fluid and the second fluid to be injected according to the diagnostic injection protocol; and for each of the one or more phases of the diagnostic injection protocol, a particular volume of the at least one of the first fluid and the second fluid therein and a flow rate at which the particular volume is to be injected into the patient during administration thereof.

Clause 7. The fluid injector system of any of clauses 1-6, wherein the first of the fluid containers comprises a syringe and the second of the fluid containers comprises a syringe.

Clause 8. A computer program product for enabling at least partial preloading into an administration line of at least one of a first fluid and a second fluid in accordance with a one or more phases of a diagnostic injection protocol, the computer program product comprising at least one non-transitory computer-readable medium comprising one or more instructions that, when executed by at least one processor, cause the at least one processor to: enable programming of the diagnostic injection protocol into a control device of a fluid injector system, the control device operably associated with at least one drive component for use in selectively actuating a plurality of fluid containers, the plurality of fluid containers capable of being placed in fluid communication with a patient through the administration line with a first of the fluid containers capable of being filled with the first fluid comprising a contrast solution and a second of the fluid containers capable of being filled with the second fluid comprising a flushing agent; and upon completion of the programming of the diagnostic injection protocol and priming of the administration line with the second fluid, enable selection and commencement of at least partial preloading into the administration line of at least one of the first fluid and the second fluid in accordance with the one or more phases of the diagnostic injection protocol.

Clause 9. The computer program product of clause 8, wherein the one or more instructions, when executed by at least one processor, further cause the at least one processor to: receive, from a user interface operably associated with the at least one processor, at least one of a plurality of user inputs associated with control of a plurality of operations of the fluid injector system, wherein a set of the plurality of user inputs is associated with the control of a corresponding set of the plurality of operations involved with the enabling of the selection and the commencement of the at least partial preloading into the administration line of the at least one of the first fluid and the second fluid in accordance with the one or more phases of the diagnostic injection protocol.

Clause 10. The computer program product of clause 8 or 9, wherein the set of the plurality of user inputs includes: a select preloading command upon entry of which into the user interface the control device readies the fluid injector system for the at least partial preloading of the diagnostic injection protocol into the administration line; a commence preloading command upon entry of which into the user interface after the select preloading command the control device actuates the plurality of fluid containers and thereby commences the at least partial preloading into the administration line of at least one of the first fluid and the second fluid in accordance with the one or more phases of the diagnostic injection protocol; and a disable preloading command upon entry of which into the user interface after the select preloading command the control device disables an effect of the select preloading command.

Clause 11. The computer program product of any of clauses 8-10, wherein the one or more instructions, when executed by at least one processor, further cause the at least one processor to: calculate a total volume of the at least one of the first fluid and the second fluid to be injected according to the diagnostic injection protocol such that, upon entry of the commence preloading command into the user interface, the at least one processor: upon determining that the total volume of the at least one of the first fluid and the second fluid to be injected according to the diagnostic injection protocol is equal to the capacity of the administration line, actuates one or more of the plurality of fluid containers and thereby preloads into the administration line the total volume of the diagnostic injection protocol in accordance with the one or more phases thereof and thereby expels from the administration line a volume of the second fluid used in the priming of the administration line therewith; upon determining that the total volume of the at least one of the first fluid and the second fluid to be injected according to the diagnostic injection protocol is less than the capacity of the administration line, actuates one or more of the plurality of fluid containers and thereby preloads into the administration line the total volume of the diagnostic injection protocol in accordance with the one or more phases thereof followed by a supplemental volume of the second fluid equal to the capacity of the administration line minus the total volume of the diagnostic injection protocol and thereby expels from the administration line the volume of the second fluid used in the priming of the administration line therewith; and upon determining that the total volume of the at least one of the first fluid and the second fluid to be injected according to the diagnostic injection protocol is greater than the capacity of the administration line, actuates one or more of the plurality of fluid containers and thereby preloads into the administration line as much of the at least one of the first fluid and the second fluid in accordance with the one or more phases of the diagnostic injection protocol as a capacity of the administration line will allow and retains within the programming a remaining portion of the diagnostic injection protocol until the diagnostic injection protocol is performed on the patient and thereby expels from the administration line the volume of the second fluid used in the priming of the administration line therewith.

Clause 12. The computer program product of any of clauses 8-11, wherein the one or more instructions, when executed by at least one processor, further cause the at least one processor to: display, via the user interface, information associated with a status of the at least partial preloading into the administration line of at least one of the first fluid and the second fluid in accordance with the one or more phases of the diagnostic injection protocol.

Clause 13. The computer program product of any of clauses 8-12, wherein the one or more instructions, when executed by at least one processor, further cause the at least one processor to: display, via the user interface, at least one of: a total volume of the at least one of the first fluid and the second fluid to be injected according to the diagnostic injection protocol; and for each of the one or more phases of the diagnostic injection protocol, a particular volume of the at least one of the first fluid and the second fluid therein and a flow rate at which the particular volume is to be injected into the patient during administration thereof.

Clause 14. The computer program product of any of clauses 8-13, wherein the first of the fluid containers comprises a syringe and the second of the fluid containers comprises a syringe.

Clause 15. A computer-implemented method for enabling at least partial preloading into an administration line of at least one of a first fluid and a second fluid in accordance with a one or more phases of a diagnostic injection protocol, the method comprising: programming, with at least one processor, the diagnostic injection protocol into a control device of a fluid injector system, the control device operably associated with at least one drive component for use in selectively actuating a plurality of fluid containers, the plurality of fluid containers capable of being placed in fluid communication with a patient through an administration line with a first of the fluid containers capable of being filled with the first fluid comprising a contrast solution and a second of the fluid containers capable of being filled with the second fluid comprising a flushing agent; and upon completion of the programming of the diagnostic injection protocol and priming of the administration line with the second fluid, enabling, with at least one processor, selection and commencement of at least partial preloading into the administration line of at least one of the first fluid and the second fluid in accordance with the one or more phases of the diagnostic injection protocol.

Clause 16. The computer-implemented method of clause 15, further comprising: receiving, from a user interface operably associated with the at least one processor, at least one of a plurality of user inputs associated with control of a plurality of operations of the fluid injector system, wherein a set of the plurality of user inputs is associated with the control of a corresponding set of the plurality of operations involved with the enabling of the selection and the commencement of the at least partial preloading into the administration line of the at least one of the first fluid and the second fluid in accordance with the one or more phases of the diagnostic injection protocol.

Clause 17. The computer-implemented method of clause 15 or 16, wherein the set of the plurality of user inputs includes: a select preloading command upon entry of which into the user interface the control device readies the fluid injector system for the at least partial preloading of the diagnostic injection protocol into the administration line; a commence preloading command upon entry of which into the user interface after the select preloading command the control device actuates the plurality of fluid containers and thereby commences the at least partial preloading into the administration line of at least one of the first fluid and the second fluid in accordance with the one or more phases of the diagnostic injection protocol; and a disable preloading command upon entry of which into the user interface after the select preloading command the control device disables an effect of the select preloading command.

Clause 18. The computer-implemented method of any of clauses 15-17, further comprising: calculating, with the at least one processor, a total volume of the at least one of the first fluid and the second fluid to be injected according to the diagnostic injection protocol such that, upon entry of the commence preloading command into the user interface, the control device: upon determining, with the at least one processor, that the total volume of the at least one of the first fluid and the second fluid to be injected according to the diagnostic injection protocol is equal to the capacity of the administration line, actuates one or more of the plurality of fluid containers and thereby preloads into the administration line the total volume of the diagnostic injection protocol in accordance with the one or more phases thereof and thereby expels from the administration line a volume of the second fluid used in the priming of the administration line therewith; upon determining, with the at least one processor, that the total volume of the at least one of the first fluid and the second fluid to be injected according to the diagnostic injection protocol is less than the capacity of the administration line, actuates one or more of the plurality of fluid containers and thereby preloads into the administration line the total volume of the diagnostic injection protocol in accordance with the one or more phases thereof followed by a supplemental volume of the second fluid equal to the capacity of the administration line minus the total volume of the diagnostic injection protocol and thereby expels from the administration line the volume of the second fluid used in the priming of the administration line therewith; and upon determining, with the at least one processor, that the total volume of the at least one of the first fluid and the second fluid to be injected according to the diagnostic injection protocol is greater than the capacity of the administration line, actuates one or more of the plurality of fluid containers and thereby preloads into the administration line as much of the at least one of the first fluid and the second fluid in accordance with the one or more phases of the diagnostic injection protocol as a capacity of the administration line will allow and retains within the programming a remaining portion of the diagnostic injection protocol until the diagnostic injection protocol is performed on the patient and thereby expels from the administration line the volume of the second fluid used in the priming of the administration line therewith.

Clause 19. The computer-implemented method of any of clauses 15-18, further comprising: displaying, with the user interface, information associated with a status of the at least partial preloading into the administration line of at least one of the first fluid and the second fluid in accordance with the one or more phases of the diagnostic injection protocol.

Clause 20. The computer-implemented method of any of clauses 15-19, further comprising: displaying, with the user interface, at least one of: a total volume of the at least one of the first fluid and the second fluid to be injected according to the diagnostic injection protocol; and for each of the one or more phases of the diagnostic injection protocol, a particular volume of the at least one of the first fluid and the second fluid therein and a flow rate at which the particular volume is to be injected into the patient during administration thereof.

Clause 21. The computer-implemented method of any of clauses 15-20, wherein the first of the fluid containers comprises a syringe and the second of the fluid containers comprises a syringe.

These and other features and characteristics of fluid injector systems, as well as computer program products and methods of operation and functions of the related elements of structures and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only.

DETAILED DESCRIPTION

Figure 1:
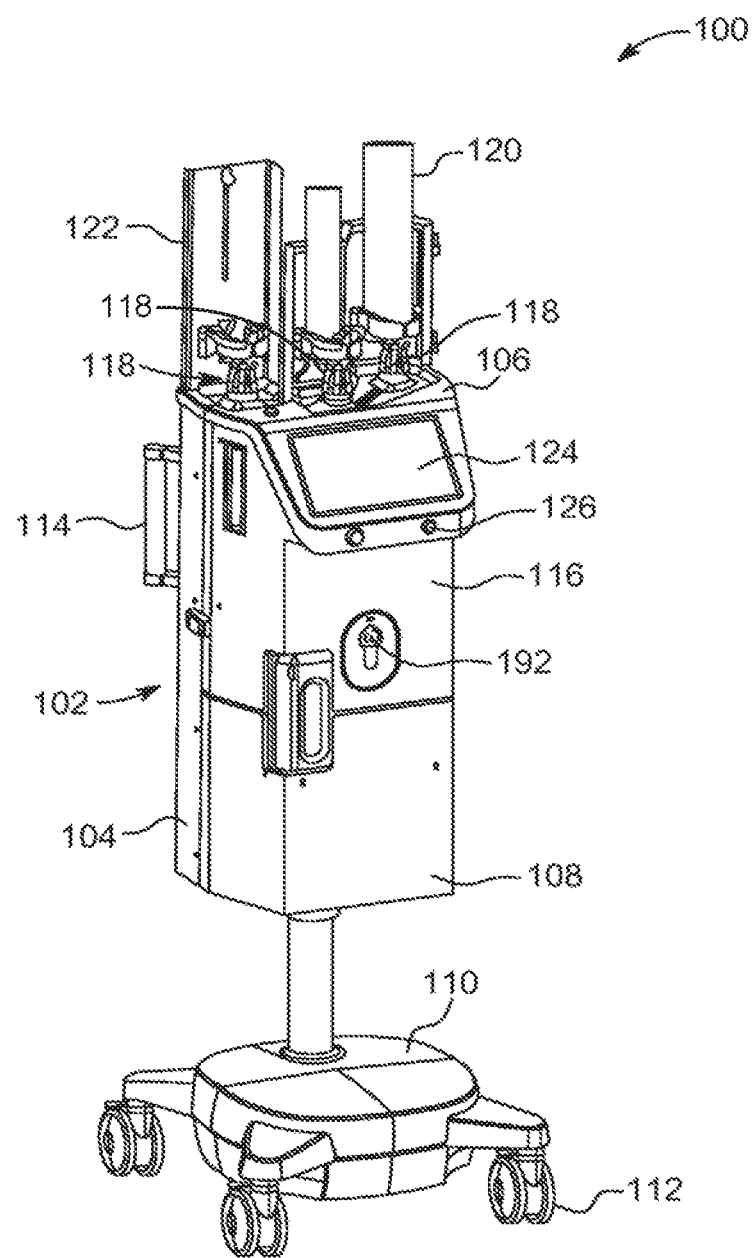
FIG. 1 is a perspective view of a multi-fluid delivery system, according to one example.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to a syringe of a multi-patient disposable set, the term "proximal" refers to a portion of a syringe nearest a piston element for delivering fluid from a syringe. When used in relation to a single-use disposable set connector, the term "distal" refers to a portion of a single-use disposable set connector nearest to a user or patient when a single-use disposable set connector is oriented for connecting with a multi-fluid injector system. When used in relation to a syringe of a fluid injector system, the term "distal" refers to a portion of a syringe nearest to a delivery nozzle. When used in relation to a single-use disposable set connector, the term "proximal" refers to a portion of a single-use disposable set connector nearest to a multi-fluid injector system when a single-use disposable set connector is oriented for connecting with a multi-fluid injector system.

It is also to be understood that the specific devices and processes illustrated in the attached drawings, and described in the following specification, are simply exemplary examples of the disclosure. Hence, specific dimensions and other physical characteristics related to the examples disclosed herein are not to be considered as limiting.

Although the present disclosure is described primarily in the context of the MEDRAD® Centargo CT Injection System, it will be apparent to persons of ordinary skill in the art that the present invention can be applied to a variety of injection systems inclusive of their associated disposables (e.g., syringes, tubing, etc.). Examples of such injection systems include the MEDRAD® Stellant CT Injection System, the MEDRAD® Stellant FLEX CT Injection System, the MEDRAD® MRXperion MR Injection System and the MEDRAD® Mark 7 Arterion Injection System offered by Bayer HealthCare LLC.

Referring to the drawings in which like reference characters refer to like parts throughout the several views thereof, the present disclosure is generally directed to a multi-fluid medical injector/injection system 100 (hereinafter "fluid injector system 100") having a multi-patient disposable set (MUDS) 130 configured for delivering fluid to a patient using a single-use disposable set (SUDS) 190 connector. The fluid injector system 100 includes multiple components as individually described herein. Generally, the fluid injector system 100 has a powered injector or other administration device and a fluid delivery set intended to be associated with the injector to deliver one or more fluids from one or more multi-dose containers under pressure into a patient, as described herein. The various devices, components, and features of the fluid injector system 100 and the fluid delivery set associated therewith are likewise described in detail herein.

With reference to FIG. 1, the fluid injector system 100 includes an injector housing 102 having opposed lateral sides 104, a distal or upper end 106, and a proximal or lower end 108. In some examples, the housing 102 may be supported on a base 110 having one or more wheels 112 for rotatable and movable support of the housing 102 on a floor surface. The one or more wheels 112 may be lockable to prevent the housing 102 from inadvertently moving once positioned at a desired location. At least one handle 114 may be provided to facilitate moving and positioning the fluid injector system 100. In other examples, the housing 102 may be removably or non-removably secured to a fixed surface, such as a floor, ceiling, wall, or other structure. The housing 102 encloses the various mechanical drive components, electrical and power components necessary to drive the mechanical drive components, and control components, such as electronic memory and electronic control devices (hereinafter electronic control device(s)), used to control operation of reciprocally movable piston elements 103 (shown in FIG. 2) associated with the fluid injector system 100 described herein. Such piston elements 103 may be reciprocally operable via electro-mechanical drive components such as a ball screw shaft driven by a motor, a voice coil actuator, a rack-and-pinion gear drive, a linear motor, and the like. In some examples, at least some of the mechanical drive components, electrical and power components, and control components may be provided on the base 110.

With continued reference to FIG. 1, the fluid injector system 100 has at least one door 116 that encloses at least some of the MUDS, the mechanical drive components, electrical and power components, and control components. The door 116 is desirably movable between an open position and a closed position (shown in FIG. 1). In some examples, the door 116 may be lockable.

The fluid injector system 100 further includes at least one bulk fluid connector 118 for connection with at least one bulk fluid source 120. In some examples, a plurality of bulk fluid connectors 118 may be provided. For example, as shown in FIG. 1, three bulk fluid connectors 118 may be provided in a side-by-side or other arrangement. In some examples, the at least one bulk fluid connector 118 may be a spike configured for removably connecting to the at least one bulk fluid source 120, such as a vial, a bottle, or a bag. The at least one bulk fluid connector 118 may have a reusable or non-reusable interface with each new bulk fluid source 120. The at least one bulk fluid connector 118 may be formed on the multi-patient disposable set, as described herein. The at least one bulk fluid source 120 may be configured for receiving a medical fluid, such as saline, contrast solution, or other medical fluid, for delivery to the fluid injector system 100. The housing 102 may have at least one support member 122 for supporting the at least one bulk fluid source 120 once it is connected to the fluid injector system 100.

With continued reference to FIG. 1, the fluid injector system 100 includes one or more user interfaces 124, such as a graphical user interface (GUI) display window. The user interface 124 may display information pertinent to a fluid injection procedure involving fluid injector system 100, such as current flow rate, fluid pressure, and volume remaining in the at least one bulk fluid source 120 connected to the fluid injector system 100 and may be a touch screen GUI that allows an operator to input commands and/or data for operation of fluid injector system 100. While the user interface 124 is shown on the injector housing 102, such user interface 124 may also be in the form of a remote display that is wired or wirelessly linked to the housing 102 and control and mechanical elements of fluid injector system 100. In some examples, the user interface 124 may be a tablet computer that is detachably connected to the housing 102 and is in wired or wirelessly linked communication with the housing 102 and control and mechanical elements of the fluid injector system 100. Additionally, the fluid injector system 100 and/or user interface 124 may include at least one control button 126 for tactile operation by an attendant operator of the fluid injector system 100. In certain examples, the at least one control button 126 may be part of a keyboard for inputting commands and/or data by the operator. The at least one control button 126 may be hard-wired to the electronic control device(s) associated with the fluid injector system 100 to provide direct input to the electronic control device(s). The at least one control button 126 may also be a graphical part of the user interface 124, such as a touch screen. In either arrangement, the at least one control button 126 desirably provides certain individual control features to the attendant operator of the fluid injector system 100, such as, but not limited to: (1) acknowledging that a multi-patient disposable set has been loaded or unloaded; (2) locking/unlocking of the multi-patient disposable set; (3) filling/purging of the fluid injector system 100; (4) inputting information and/or data related to the patient and/or injection procedure; (5) preloading the fluid injector system 100; and (6) initiating/stopping an injection procedure. The user interface 124 and/or any electronic processing units associated with the fluid injector system 100 may be wired or wirelessly connected to an operation and/or data storage system such as a hospital network system.

Figure 2:
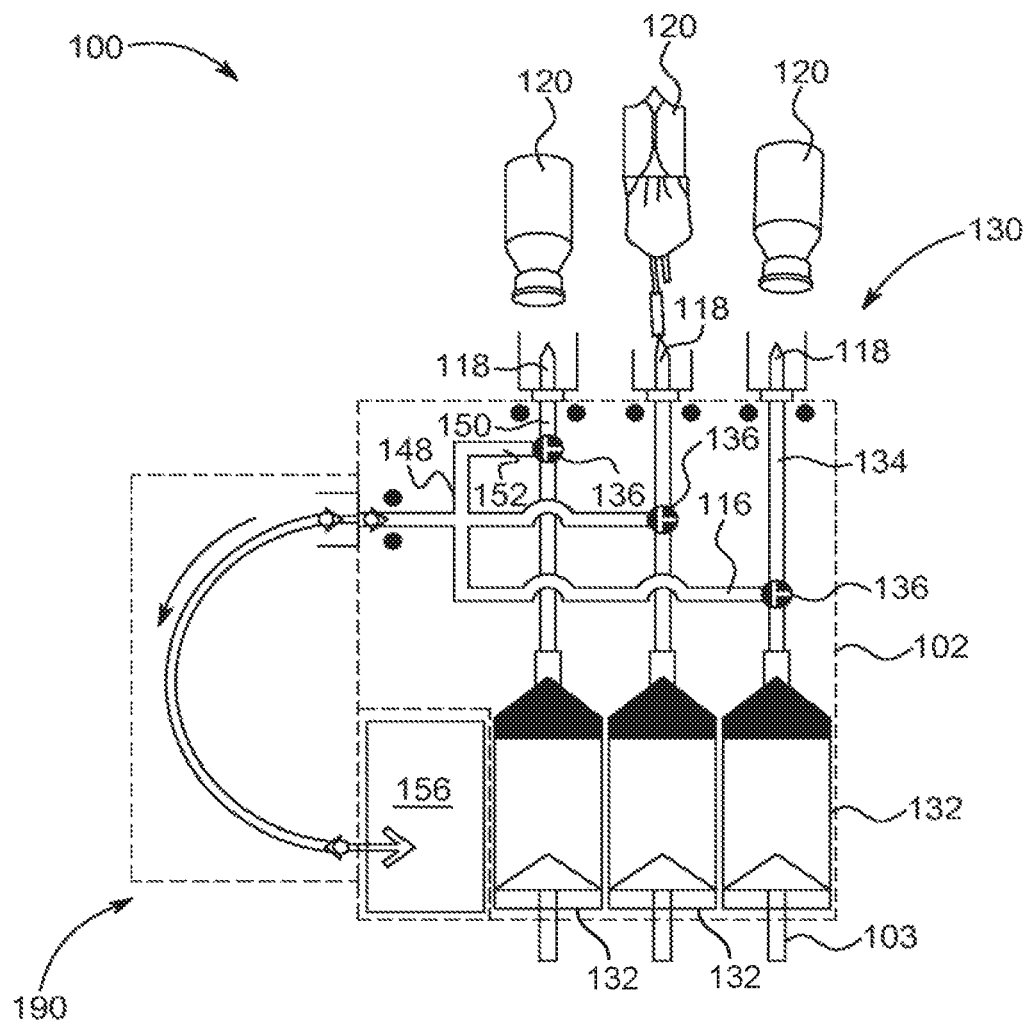
FIG. 2 is schematic view of various fluid paths within the multi-fluid delivery system of FIG. 1.

With reference to FIG. 2, the fluid injector system 100 includes a MUDS 130 that is removably connected to the fluid injector system 100 for delivering one or more fluids from the one or more bulk fluid sources 120 to the patient. Examples and features of the MUDS are further described in International Patent Application Publication No. WO 2016/112163, filed on Jan. 7, 2016 and entitled "Multiple Fluid Delivery System with Multi-Use Disposable Set and Features Thereof", the disclosure of which is incorporated herein by reference in its entirety. The MUDS 130 may include one or more syringes or pumps 132. In some examples, the number of syringes 132 may correspond to the number of bulk fluid sources 120. For example, with reference to FIG. 2, the MUDS 130 has three syringes 132 in a side-by-side arrangement such that each syringe 132 is fluidly connectable to one or more of the bulk fluid sources 120. In some examples, one or two bulk fluid sources 120 may be connected to one or more syringes 132 of the MUDS 130. Each syringe 132 may be fluidly connectable to one of the bulk fluid sources 120 by a corresponding bulk fluid connector 118 and an associated MUDS fluid path 134. The MUDS fluid path 134 may have a spike element that connects to the bulk fluid connector 118. In some examples, the bulk fluid connector 118 may be provided directly on the MUDS 130.

With further reference to FIG. 2, the MUDS 130 is removably connectable to the housing 102 of the fluid injector system 100. As will be appreciated by one having ordinary skill in the art, it may be desirable to construct at least a portion of the MUDS 130 from a clear medical grade plastic in order to facilitate visual verification that a fluid connection has been established with the fluid injector system 100. Visual verification is also desirable for confirming that no air bubbles are present within various fluid connections. Alternatively, at least a portion of the MUDS 130 and/or door 116 may include windows (not shown) for visualization of the connection between various components. Various optical sensors (not shown) may also be provided to detect and verify the connections. Additionally, various lighting elements (not shown), such as light emitting diodes (LEDs), may be provided to actuate one or more optical sensors and indicate that a suitable connection has been established between the various components.

With specific reference to FIG. 2, a schematic view of various fluid paths of the fluid injector system 100 is provided. The MUDS 130 may include one or more valves 136, such as stopcock valves, for controlling which medical fluid or combinations of medical fluids are withdrawn from the multi-dose bulk fluid source 120 and/or are delivered to a patient through each syringe 132. In some examples, the one or more valves 136 may be provided on a distal end of the plurality of syringes 132 or on a manifold 148. The manifold 148 may be in fluid communication via valves 136 and/or syringes 132 with a first end of the MUDS fluid path 134 that connects each syringe 132 to the corresponding bulk fluid source 120. The opposing second end of the MUDS fluid path 134 may be connected to the respective bulk fluid connector 118 that is configured for fluidly connecting with the bulk fluid source 120. Depending on the position of the one or more valves 136, fluid may be drawn into the one or more syringes 132 or it may be delivered from the one or more syringes 132. In a first position, such as during the filling of the syringes 132, the one or more valves 136 are oriented such that fluid flows from the bulk fluid source 120 into the desired syringe 132 through a fluid inlet line 150, such as a MUDS fluid path. During the filling procedure, the one or more valves 136 are positioned such that fluid flow through one or more fluid outlet lines 152 or manifold 148 is blocked. In a second position, such as during a fluid delivery procedure, fluid from one or more syringes 132 is delivered to the manifold 148 through the one or more fluid outlet lines 152 or syringe valve outlet ports. During the delivery procedure, the one or more valves 136 are positioned such that fluid flow through one or more fluid inlet lines 150 is blocked. The one or more valves 136, fluid inlet lines 150, and/or fluid outlet lines 152 may be integrated into the manifold 148. The one or more valves 136 may be selectively positioned to the first or second position by manual or automatic handling. For example, the operator may position the one or more valves 136 into the desired position for filling or fluid delivery. In other examples, at least a portion of the fluid injector system 100 is operable for automatically positioning the one or more valves 136 into a desired position for filling or fluid delivery based on input by the operator, as described herein.

With continued reference to FIG. 2, in some examples, the fluid outlet line 152 may also be connected to a waste reservoir 156 of the fluid injector system 100. The waste reservoir 156 is desirably separate from the syringes 132 to prevent contamination. In some examples, the waste reservoir 156 is configured to receive waste fluid expelled from the syringes 132 during, for example, a flushing, priming, or preloading operation. The waste reservoir 156 may be removable from the housing 102 in order to dispose of the contents of the waste reservoir 156. In other examples, the waste reservoir 156 may have a draining port (not shown) for emptying the contents of the waste reservoir 156 without removing the waste reservoir 156 from the housing 102. In some examples, the waste reservoir 156 is provided as a separate component from the MUDS 130.

Having generally described the components of the fluid injector system 100 and the MUDS 130, the structure and method of use of a single-use disposable set (SUDS) 190 and its interaction with MUDS 130 will now be described.

Figure 3A:
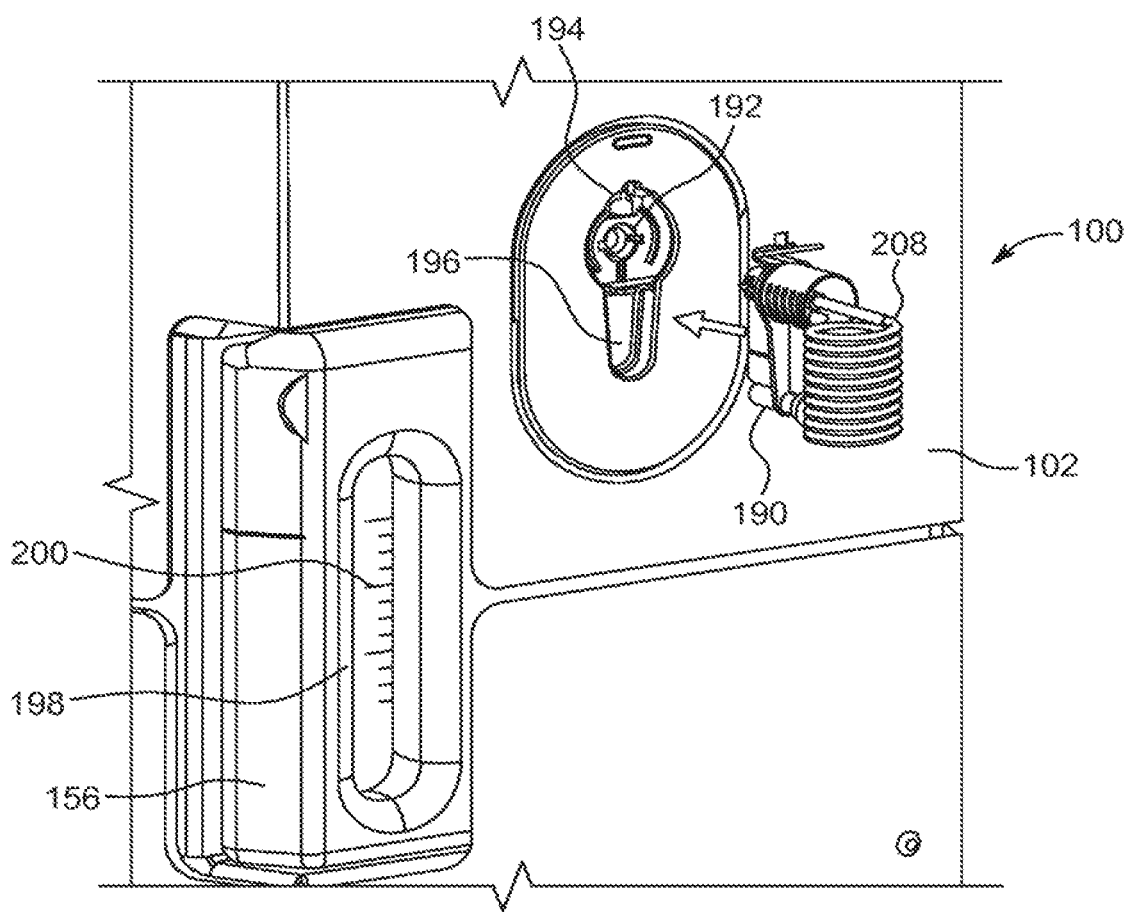
FIG. 3A is a perspective view of a connection interface prior to connecting a single-use disposable set (SUDS) connector with a multi-fluid delivery system.
Figure 3B:
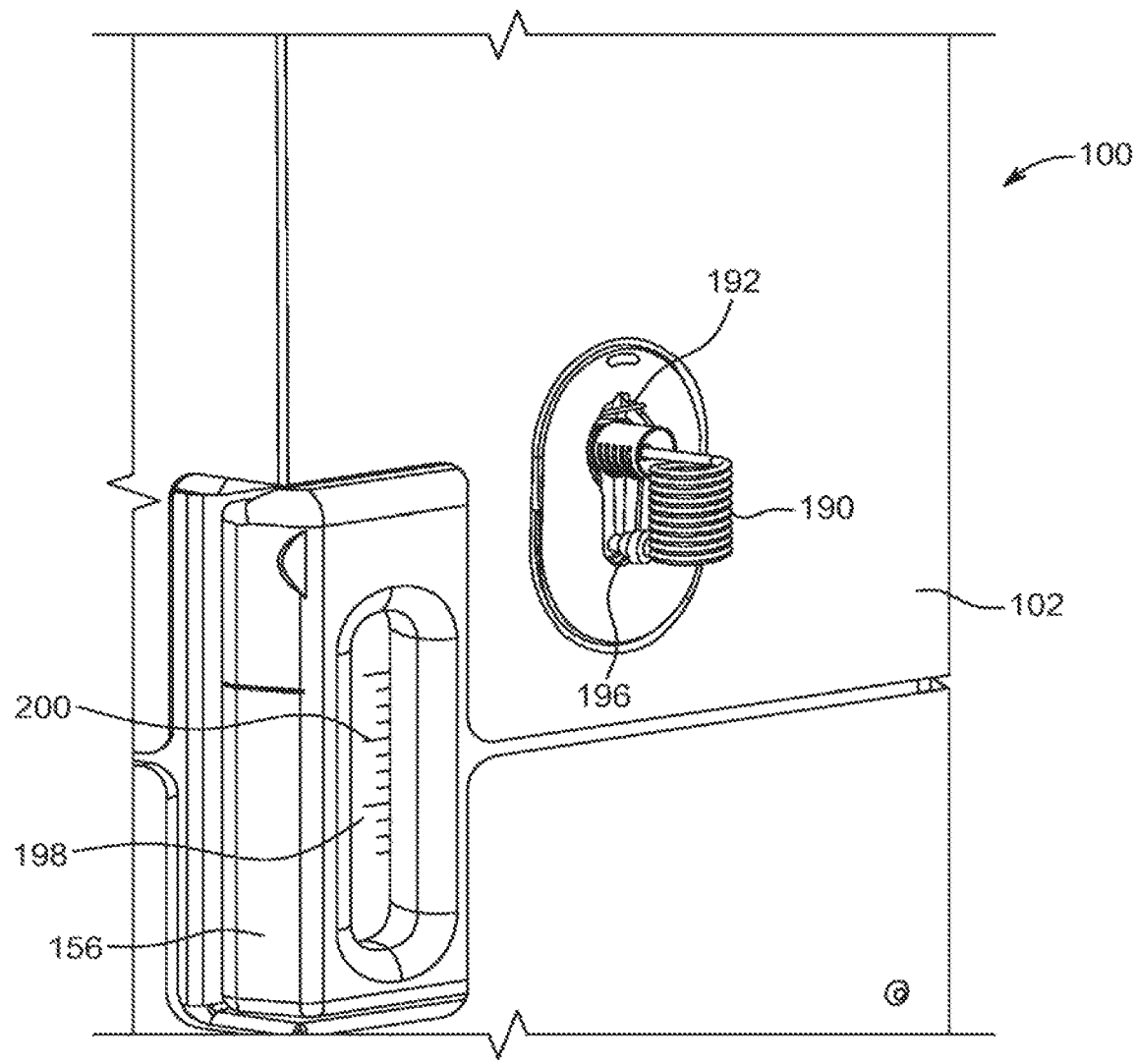
FIG. 3B is a perspective view of the connection interface of FIG. 3A showing the SUDS connector connected with the multi-fluid delivery system.

With reference to FIGS. 3A and 3B, the fluid injector system 100 has a connection port 192 that is configured to form a releasable fluid connection with at least a portion of the SUDS 190. In some examples, the connection port 192 may be formed on the MUDS 130. The connection port 192 may be shielded by at least a portion of the housing 102 of the fluid injector system 100. For example, recessing the connection port 192 within the interior of the housing 102 may preserve the sterility of the connection port 192 by preventing or limiting a user or patient from touching and contaminating the portions of the connection port 192 that contact the fluid to be injected into the patient. In some examples, the connection port 192 is recessed within an opening 194 formed on the housing 102 of the fluid injector system 100, or the connection port 192 may have a shielding structure (not shown) that surrounds at least a portion of the connection port 192. In other examples, the connection port 192 may be formed directly on the housing 102 and connected to the MUDS 130 by a fluid path (not shown). As described herein, the SUDS 190 may be connected to the connection port 192, formed on at least a portion of the MUDS 130 and/or the housing 102. Desirably, the connection between the SUDS 190 and the connection port 192 is a releasable connection to allow the SUDS 190 to be selectively disconnected from the connection port 192 (FIG. 3A) and connected to the connection port 192 (FIG. 3B). In some examples, the SUDS 190 may be disconnected from the connection port 192 and disposed after each fluid delivery procedure, and a new SUDS 190 may be connected to the connection port 192 for a subsequent fluid delivery procedure.

With continued reference to FIGS. 3A and 3B, a waste inlet port 196 may be provided separately from the connection port 192. The waste inlet port 196 is in fluid communication with the waste reservoir 156. In some examples, the waste reservoir 156 is provided separately from the SUDS 190 such that the fluid from the waste inlet port 196 can be delivered to the waste reservoir 156. At least a portion of the SUDS 190 may be releasably connected to or associated with the waste inlet port 196 for introducing waste fluid into the waste reservoir 156 during, for example, a priming operation that expels air from the SUDS 190. The waste reservoir 156 may have a viewing window 198 with indicia 200, such as graduated markings, that indicate the fill level of the waste reservoir 156.

Figure 4A:
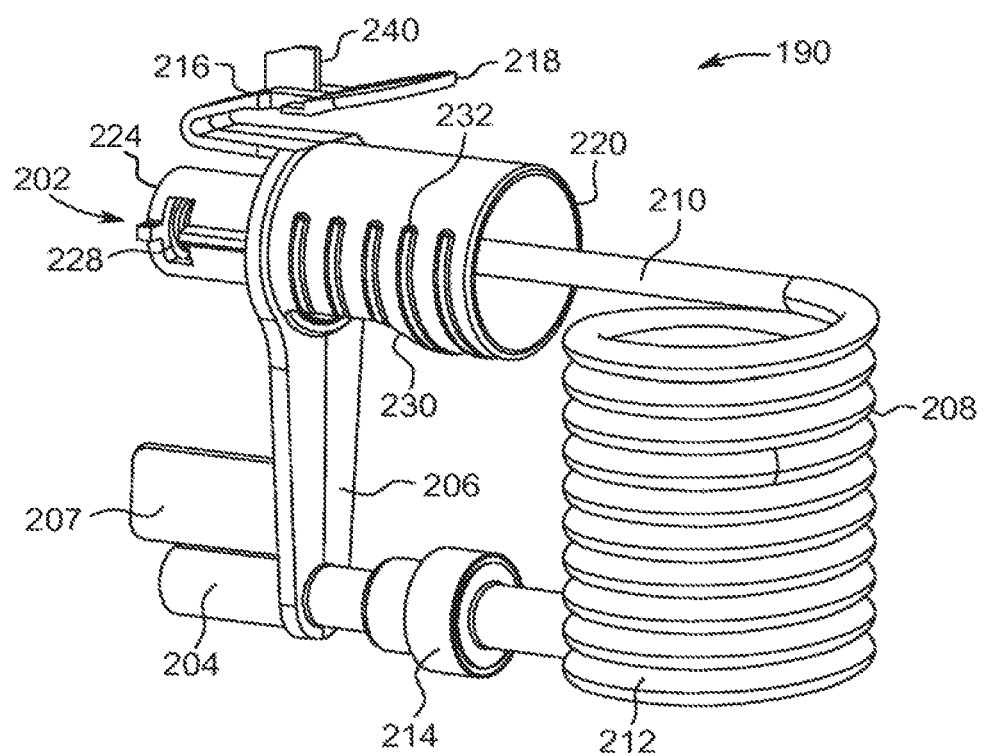
FIG. 4A is an enlarged, perspective view of the SUDS connector shown in FIGS. 3A and 3B.
Figure 4B:
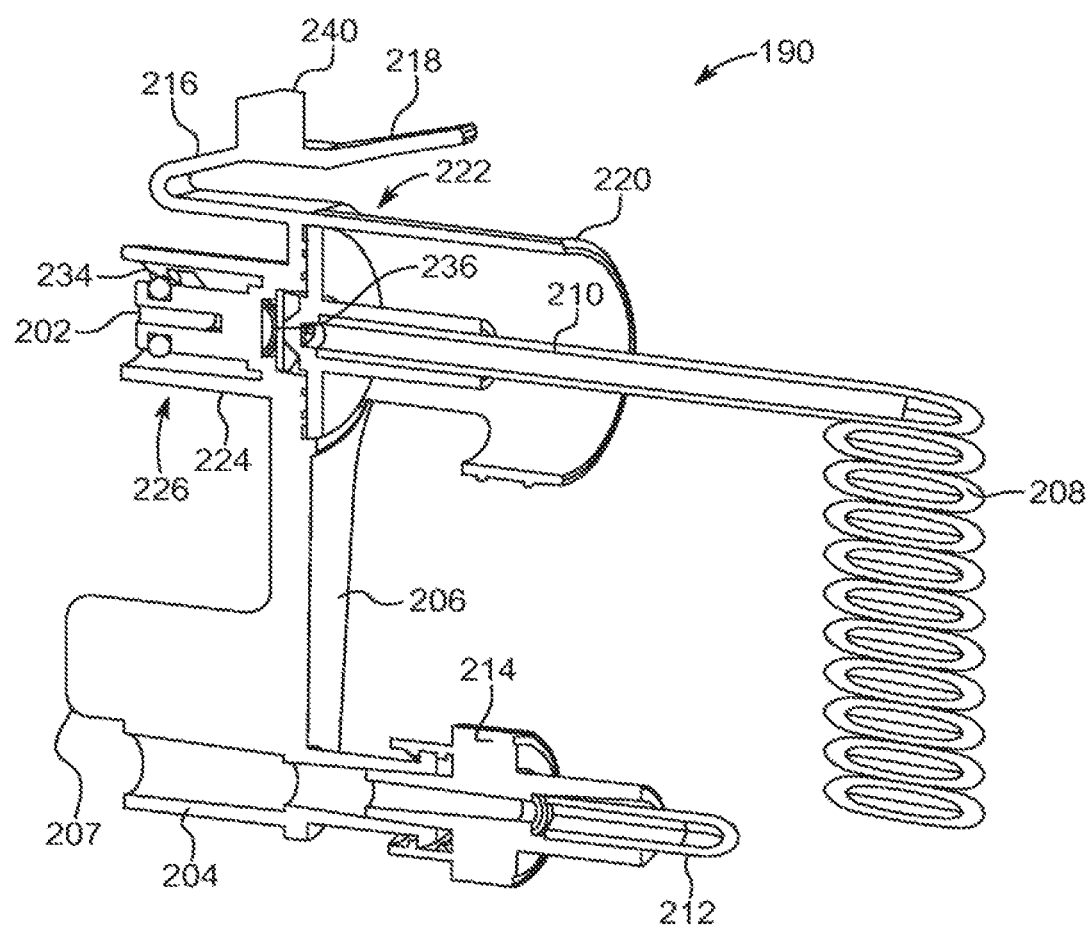
FIG. 4B is a longitudinal cross-sectional view of the SUDS connector shown in FIG. 4A.

With reference to FIG. 4A, the SUDS 190 has a fluid inlet port 202 that is configured for releasable connection with the connection port 192 (shown in FIG. 3A). The fluid inlet port 202 receives fluid delivered from the fluid injector system 100. The fluid inlet port 202 is desirably a hollow, tubular structure, as shown in FIG. 4B. The SUDS 190 further has a waste outlet port 204 that is configured for releasable connection or association with the waste inlet port 196 (shown in FIG. 3A). The waste outlet port 204 receives waste fluid and delivers such waste fluid to the waste reservoir 156 during, for example, a priming or flushing operation of the SUDS 190. The waste outlet port 204 is desirably a hollow, tubular structure, as shown in FIG. 4B. The waste outlet port 204 may be connected to, inserted into, or located in the waste inlet port 202 so that the waste fluid may flow through the waste inlet port 202 and continue into waste reservoir 156. The fluid inlet port 202 and the waste outlet port 204 may be spaced apart from each other by a spacer 206. In some examples, the spacer 206 is dimensioned to position the fluid inlet port 202 and the waste outlet port 204 for alignment with the connection port 192 and the waste inlet port 196, respectively. It is noted that the SUDS 190 is shown in FIG. 4A in a state after removal from packaging (not shown). Prior to use, the SUDS 190 is desirably packaged in a pre-sterilized, sealed package that protects the SUDS 190 from contamination with airborne or surface-borne contaminants. Alternatively, the sealed package and the SUDS 190 may be sterilized after packaging.

The SUDS 190 desirably has an asymmetrical structure, so that the user can only attach the SUDS 190 to the MUDS 130 in one orientation. In this manner, the user is prevented from attaching the fluid inlet port 202 to the waste inlet port 196. In some examples, a fin 207 may be provided on at least a portion of the SUDS 190 to prevent erroneous insertion of the SUDS 190 in the connection port 192. In certain examples, the fin 207 may be formed on the spacer 206 proximate to the waste outlet port 204. In this manner, the fin 207 may interfere with the incorrect insertion of the SUDS 190 into the connection port 192. Structures and shapes other than fin 207 may be used to prevent erroneous insertion of the SUDS 190 into connection port 192.

Figure 4C:
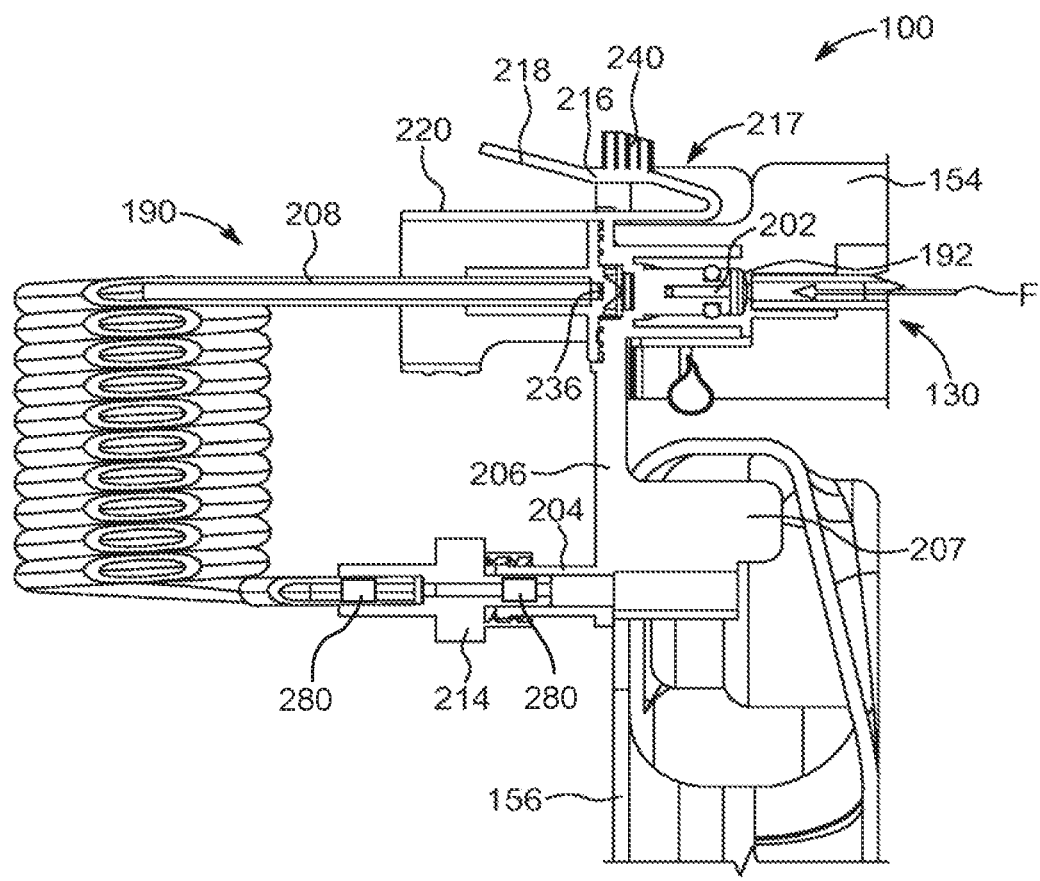
FIG. 4C is a partial cross-sectional view of the SUDS connector shown in FIGS. 4A-4B connected to a port of a multi-fluid delivery system.

In some examples, tubing 208, also referred to as an administration line, may be connected at its proximal end 210 to the fluid inlet port 202. The tubing 208 is configured to deliver fluid received from the fluid inlet port 202. The distal end 212 of the tubing 208 may have a connector 214, which may include a one-way check valve, that is configured for connection with the waste outlet port 204 or a fluid path connected to the patient (not shown). The tubing 208 may be made from a flexible material, such as a medical grade plastic material, that allows the tubing 208 to be coiled. The connector 214 may be a luer-lock connector (either a male luer-lock connector or a female luer-lock connector depending on the desired application) or other medical connector configuration. In some examples, the connector 214 may include at least one one-way check valve 280 therein, as shown in FIG. 4C, to prevent backflow of fluid. Alternatively, a one-way check valve may be located elsewhere in the SUDS 190 between fluid inlet port 202 and connector 214.

With continued reference to FIG. 4A, the SUDS 190 may have a locking tab 216 that is configured for selectively locking the SUDS 190 with the fluid injector system 100 depending on the engagement of the locking tab 216 with at least a portion of the fluid injector system 100. In some examples, the locking tab 216 may be a flexible tab that is deflectable between an engaged position and a disengaged position by deflecting at least a portion of the locking tab 216. The locking tab 216 may have a pressing surface 218 that, when pressed, causes the locking tab 216 to be deflected from the engaged position to the disengaged position for insertion and removal of the SUDS 190 from the fluid injector system 100. In some examples, the locking tab 216 may be configured for releasable locking engagement with a receiving slot 217 on the MUDS 130 (shown in FIG. 4C).

With reference to FIG. 4B, the SUDS 190 may have a first annular skirt 224 extending circumferentially around a proximal end 226 of the fluid inlet port 202 and a second annular skirt 220 extending circumferentially around a distal end 222 of the fluid inlet port 202. The first and second annular skirts 224, 220 surround the fluid inlet port 202 to prevent inadvertent contact and contamination. The first annular skirt 224 may have one or more recesses 228 (shown in FIG. 4A) extending through a sidewall thereof. The one or more recesses 228 may provide a locking interface with a corresponding locking element (not shown) on the fluid injector system 100. The second annular skirt 220 may have at least one indentation 230 (shown in FIG. 4A) to facilitate grasping and handling of the SUDS 190. In some examples, the second annular skirt 220 may have a textured surface having one or more ribs to facilitate gripping and handling of the SUDS 190.

With continued reference to FIG. 4B, at least one annular seal 234 may be provided around the proximal end 226 of the fluid inlet port 202. The at least one annular seal 234 may seal the fluid inlet port 202 to prevent fluid from leaking through the SUDS 190. The at least one annular seal 234 may provide a fluid seal between the SUDS 190 and the MUDS 130 when they are fluidly connected with one another to allow fluid to flow from the MUDS 130 to the SUDS 190 without leaking. A one-way check valve 236 may be provided within a lumen of the fluid inlet port 202 to prevent fluid from flowing in a reverse direction from the SUDS 190 into the MUDS 130.

With reference to FIG. 4C, the SUDS 190 shown in FIG. 4A is shown connected to the fluid injector system 100. While FIG. 4C illustrates the connection port 192 formed on the MUDS 130, in other examples, the connection port 192 may be formed on a portion of the housing 102 (shown in FIG. 1). The fluid inlet port 202 of the SUDS 190 is connected to the connection port 192 to establish a fluid path in a direction of arrow F shown in FIG. 4C. Fluid passing through the fluid inlet port 202 flows through the one-way valve 236 and into tubing 208. Any fluid that may drip from the interface between the fluid inlet port 202 and the connection port 192 is collected in the waste reservoir 156. The waste reservoir 156 may be shaped to collect any fluid that may drip from the SUDS 190 when it is removed from the MUDS 130. Additionally, when the SUDS 190 is connected to the connection port 192, the outlet of the waste outlet port 204 is positioned within the waste inlet port 196 such that waste fluid from the tubing 208 may be discharged into the waste reservoir 156. The spacer 206 may define an insertion stop surface to define the depth of insertion of the SUDS 190 into the connection port 192.

Figure 5:
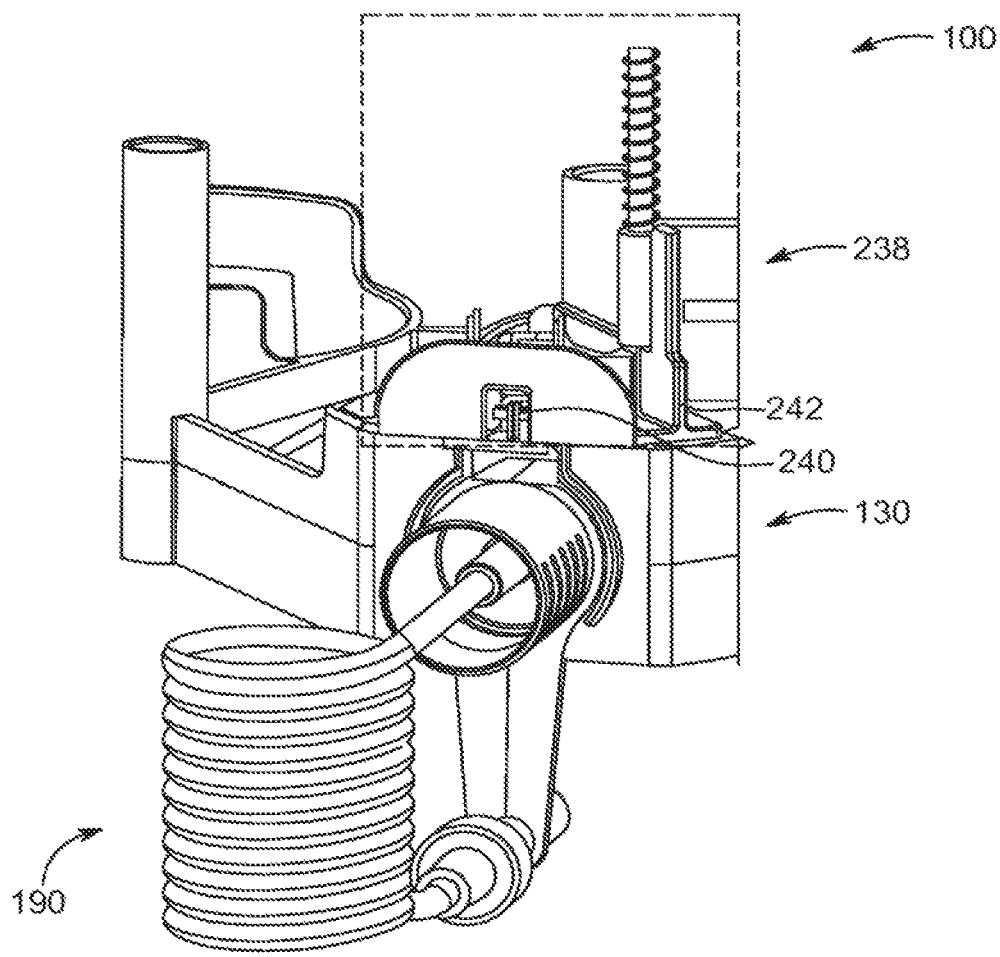
FIG. 5 is a perspective view of the SUDS connector shown in FIG. 4C with a portion of the multi-fluid delivery system and a multi-patient disposable set (MUDS) connected thereto cutaway.

With reference to FIG. 5, the fluid injector system 100 may have a sensor system 238 adapted to identify when the SUDS 190 is in fluid communication with the MUDS 130. The sensor system 238 may include at least one sensing element, such as a sensor fin 240, on the SUDS 190 and a corresponding sensor 242 on the fluid injector system 100 or MUDS 130. The sensor 242 may be configured to detect the presence and absence of the at least one sensor fin 240 or other sensing element. In some examples, the sensing element, such as the at least one sensor fin 240, is formed on the locking tab 216 of the SUDS 190, such as shown in FIG. 4A. In other examples, the sensing element, such as the at least one sensor fin 240, may be formed on any portion of the SUDS 190. The sensor 242 may be an optical sensor that is seated and secured within a respective mount formed on the housing 102 of the fluid injector system 100. As will be appreciated by those versed in the field of powered medical fluid injectors, the sensor 242 may be electronically coupled to an electronic control device used to discretely control operation of the fluid injector system, such as the operation of the one or more piston elements, based, at least in part, on input from the sensor 242. The sensing element, such as the sensor fin 240 may have one or more reflective surfaces that reflect visible or infrared light to be detected by the sensor 242. In other examples, mechanical interaction between the sensing element and the sensor 242 may be used.

In some examples, the SUDS 190 may further include reuse prevention features. For example, the SUDS 190 may include one or more breakable sensor elements, tabs, or structures that fold or break when the SUDS 190 is removed from the MUDS 130. Absence of these features may prevent reinsertion and reuse of the SUDS 190 after removal. In this manner, it can be assured that the SUDS 190 is only used for one fluid delivery procedure.

Other examples and features of the SUDS 190 are described in U.S. Patent Application Publication No. 2016/0331951, filed Jul. 7, 2016 and entitled "Single-Use Disposable Set Connector", the disclosure of which is incorporated herein by reference in its entirety.

Having generally described the components of the fluid injector system 100, the MUDS 130, and the SUDS 190, a method of operation of using the SUDS 190 will now be described in detail. In use, a medical technician or user removes the disposable SUDS 190 from its packaging (not shown) and inserts the fluid inlet port 202 into the connection port 192 on the MUDS 130. As described above, the SUDS 190 must be inserted in the correct orientation such that the fluid inlet port 202 is aligned for connection with the connection port 192 and the waste outlet port 204 is aligned for connection with the waste inlet port 196. The SUDS 190 may be secured to the MUDS 130 by inserting the locking tab 216 into the receiving slot 217 on the MUDS 130. Once the SUDS 190 is securely connected to the MUDS 130, for example as sensed by the sensor 242, the fluid injector system 100 (shown in FIG. 1) draws fluid into one or more of the plurality of syringes 132 of the MUDS 130 and performs an automatic priming or flushing operation for removing air from the MUDS 130 and the SUDS 190. During such priming or flushing operation, fluid from the MUDS 130 is injected through the connection port 192 and into the tubing 208 of the SUDS 190. The fluid flows through the tubing 208, the connector 214 and through the waste outlet port 204 and into the waste reservoir 156. Once the automatic priming or flushing operation is completed, the tubing 208 may optionally be preloaded by injecting fluid from the MUDS 130 through the connection port 192. Additional details of the preloading operation will be described later in greater detail. After the automatic priming or flushing operation and, optionally, the preloading operation are completed, the medical technician disconnects the connector 214 from the waste outlet port 204. The connector 214 may then be connected to the patient via a catheter, vascular access device, needle, or additional fluid path set to facilitate fluid delivery to the patient. Once the fluid delivery is completed, the SUDS 190 is disconnected from the patient and the MUDS 130 by disengaging the locking tab 216 of the SUDS 190 from the receiving slot 217 on the MUDS 130. The medical technician may then dispose of the SUDS 190. In certain examples, removing the SUDS 190 from the MUDS 130 causes reuse prevention features (not shown) to activate, thereby preventing reinsertion and reuse of the SUDS 190.

Figure 6:
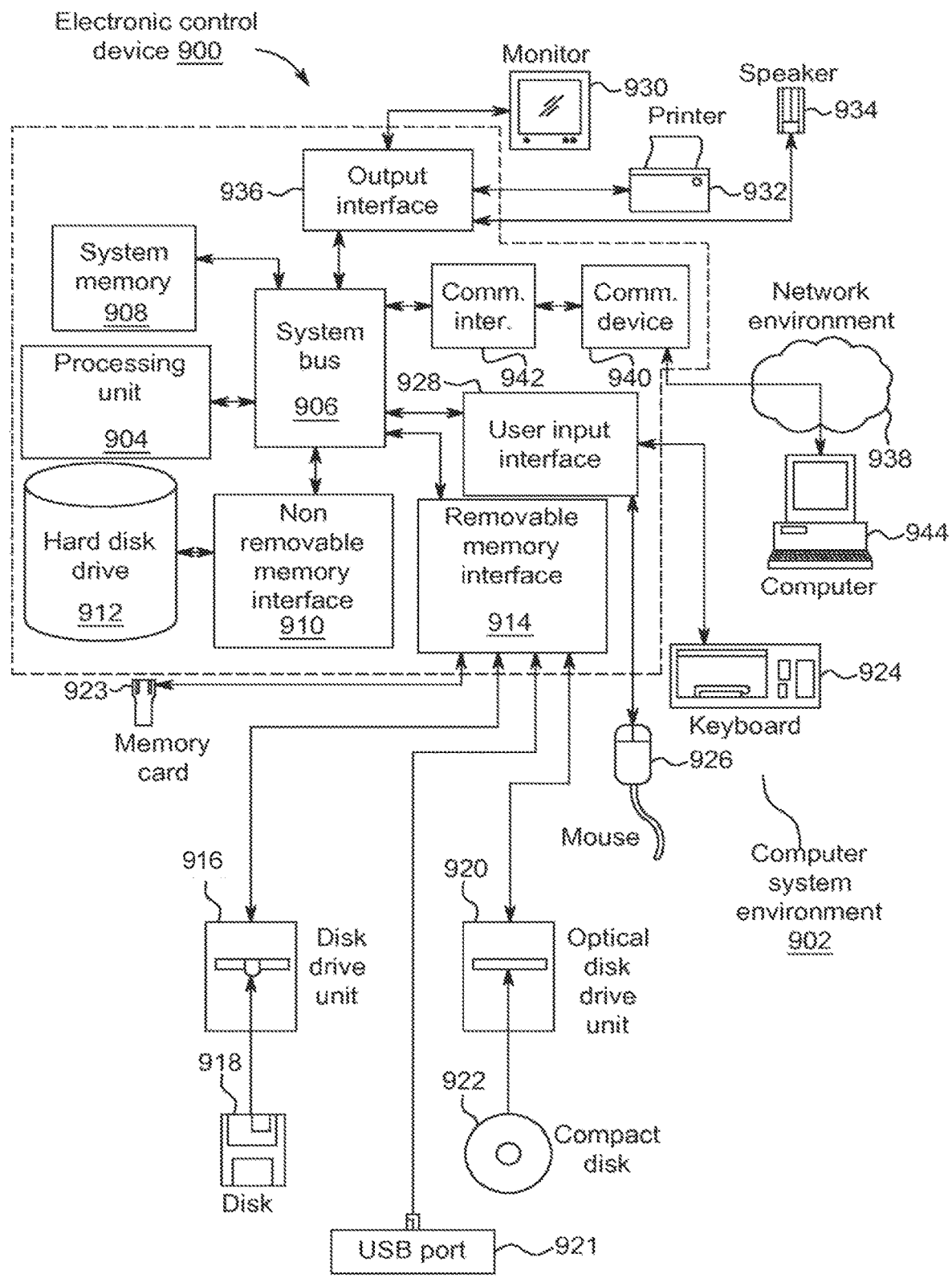
FIG. 6 is a schematic view of an electronic control system of a multi-fluid delivery system in accordance with another example.

With reference to FIG. 6, an electronic control device 900 may be associated with fluid injector system 100 to control the filling and delivery operations. In some examples, the electronic control device 900 may control the operation of various valves, piston members, and other elements to effect a desired filling or delivery procedure. For example, the electronic control device 900 may include a variety of discrete computer-readable media components. For example, this computer-readable media may include any media that can be accessed by the electronic control device 900, such as volatile media, non-volatile media, removable media, non-removable media, transitory media, non-transitory media, etc. As a further example, this computer-readable media may include computer storage media, such as media implemented in any method or technology for storage of information, such as computer-readable instructions, data structures, program modules, or other data; random access memory (RAM), read-only memory (ROM), electrically erasable programmable read-only memory (EEPROM), flash memory, or other memory technology; CD-ROM, digital versatile disks (DVDs), or other optical disk storage; magnetic cassettes, magnetic tape, magnetic disk storage, or other magnetic storage devices; or any other medium which can be used to store the desired information and which can be accessed by the electronic control device 900. Further, this computer-readable media may include communications media, such as computer-readable instructions, data structures, program modules, or other data in a modulated data signal, such as a carrier wave or other transport mechanism and include any information delivery media, wired media (such as a wired network and a direct-wired connection), and wireless media (such as acoustic signals, radio frequency signals, optical signals, infrared signals, biometric signals, bar code signals, etc.). Of course, combinations of any of the above should also be included within the scope of computer-readable media.

The electronic control device 900 further includes a system memory 908 with computer storage media in the form of volatile and non-volatile memory, such as ROM and RAM. A basic input/output system (BIOS) with appropriate computer-based routines assists in transferring information between components within the electronic control device 900 and is normally stored in ROM. The RAM portion of the system memory 908 typically contains data and program modules that are immediately accessible to or presently being operated on by a processor 904, e.g., an operating system, application programming interfaces, application programs, program modules, program data, and other instruction-based computer-readable codes.

With continued reference to FIG. 6, the electronic control device 900 may also include other removable or non-removable, volatile or non-volatile, transitory or non-transitory computer storage media products. For example, the electronic control device 900 may include a non-removable memory interface 910 that communicates with and controls a hard disk drive 912, e.g., a non-removable, non-volatile magnetic medium; and a removable, non-volatile memory interface 914 that communicates with and controls a magnetic disk drive unit 916 (which reads from and writes to a removable, non-volatile magnetic disk 918), an optical disk drive unit 920 (which reads from and writes to a removable, non-volatile optical disk 922, such as a CD ROM), a Universal Serial Bus (USB) port 921 for use in connection with a removable memory card, etc. However, it is envisioned that other removable or non-removable, volatile or non-volatile computer storage media can be used in an exemplary computing system environment 902, including, but not limited to, magnetic tape cassettes, DVDs, digital video tape, solid state RAM, solid state ROM, etc. These various removable or non-removable, volatile or non-volatile magnetic media are in communication with the processor 904 and other components of the electronic control device 900 via a system bus 906. The drives and their associated computer storage media, discussed above and illustrated in FIG. 6, provide storage of operating systems, computer-readable instructions, application programs, data structures, program modules, program data, and other instruction-based, computer-readable code for the electronic control device 900 (whether duplicative or not of this information and data in the system memory 908).

A user may enter commands, information, and data into the electronic control device 900 through certain attachable or operable input devices, such as the user interface 124 shown in FIG. 1, via a user input interface 928. A variety of such input devices may be utilized, e.g., a microphone, a trackball, a joystick, a touchpad, a touch-screen, a scanner, etc., including any arrangement that facilitates the input of data and information to the electronic control device 900 from an outside source. As discussed, these and other input devices are often connected to the processor 904 through the user input interface 928 coupled to the system bus 906, but may be connected by other interface and bus structures, such as a parallel port, game port, or a USB. Still further, data and information can be presented or provided to a user in an intelligible form or format through certain output devices, such as a monitor 930 (to visually display this information and data in electronic form), a printer 932 (to physically display this information and data in print form), a speaker 934 (to audibly present this information and data in audible form), etc. All of these devices are in communication with the electronic control device 900 through an output interface 936 coupled to the system bus 906. It is envisioned that any such peripheral output devices be used to provide information and data to the user.

The electronic control device 900 may operate in a network environment 938 through the use of a communications device 940, which is integral to the electronic control device 900 or remote therefrom. This communications device 940 is operable by and in communication with the other components of the electronic control device 900 through a communications interface 942. Using such an arrangement, the electronic control device 900 may connect with or otherwise communicate with one or more remote computers, such as a remote computer 944, which may be a personal computer, a server, a router, a network personal computer, a peer device, or other common network nodes, and typically includes many or all of the components described above in connection with the electronic control device 900. Using appropriate communication devices 940, e.g., a modem, a network interface or adapter, etc., the computer 944 may operate within and communicate through a local area network (LAN) and a wide area network (WAN), but may also include other networks such as a virtual private network (VPN), an office network, an enterprise network, an intranet, the Internet, etc.

As used herein, the electronic control device 900 includes or is operable to execute appropriate custom-designed or conventional software to perform and implement the processing steps of the method and system of the present disclosure, thereby forming a specialized and particular computing system. Accordingly, the method and system may include one or more electronic control devices 900 or similar computing devices having a computer-readable storage medium capable of storing computer-readable program code or instructions that cause the processor 904 to execute, configure, or otherwise implement the methods, processes, and transformational data manipulations discussed hereinafter in connection with the present disclosure. Still further, the electronic control device 900 may be in the form of a personal computer, a personal digital assistant, a portable computer, a laptop, a palmtop, a mobile device, a mobile telephone, a server, or any other type of computing device having the necessary processing hardware to appropriately process data to effectively implement the fluid injector system, the computer program product and the computer-implemented method of the present disclosure.

It will be apparent to one skilled in the relevant arts that the system may utilize databases physically located on one or more computers which may or may not be the same as their respective servers. For example, programming software on electronic control device 900 can control a database physically stored on a separate processor of the network or otherwise.

In some examples, the electronic control device 900 may be programmed so that automatic refill occurs based upon a preprogrammed trigger minimum volume in the respective syringes 132. For example, when the volume of fluid remaining in at least one of the syringes 132 is less than a programmed volume, a syringe refill procedure is automatically initiated by the electronic control device 900. The electronic control device 900 associated with the fluid injector system 100 may determine that the preprogrammed trigger minimum volume has been reached by tracking the fluid volume dispensed from the respective syringes 132 during operation of the fluid injector system 100. Alternatively, fluid level sensors may be incorporated into the fluid injector system 100 and inputs from these fluid level sensors may be provided to the electronic control device 900 so that the electronic control device 900 may determine when the preprogrammed trigger minimum volume has been reached in at least one of the syringes 132. The fill volume and rate of refill can be preprogrammed in the electronic control device 900. The automatic refill procedure can be stopped either automatically by the electronic control device 900 or may be manually interrupted. In addition, an automatic refill procedure may be initiated when, at the completion of a fluid injection procedure, there is not enough fluid in at least one of the syringes 132 to perform the next programmed fluid injection procedure.

During a refill procedure it is possible that one or more of the bulk fluid sources 120 associated with the respective syringes 132 may become empty (e.g., initially lack sufficient fluid to complete a full refill of the one or more syringes 132). A replacement bulk fluid source 120 is, therefore, necessary and replacement of such bulk fluid source 120 is desirably made quickly. The fluid injector system 100 may have an indicator, such as an audible and/or visual indicator, to indicate to the operator that a change of the bulk fluid source 120 is necessary before the fluid injector system 100 may be used.

As described above, the fluid injector system 100 may automatically prime the MUDS 130 and the SUDS 190 once the SUDS 190 is securely connected to the MUDS 130, for example, as sensed by the sensor 242. During such a priming operation, saline, or another suitable flushing agent, from the MUDS 130 is injected through the connection port 192, into the tubing 208 of the SUDS 190, and into the waste reservoir 156. Saline flow toward the waste reservoir 156 purges air from the fluid injector system by forcing any air in the MUDS 130 and the SUDS 190 out the distal end 212 of the tubing 208. Saline thus displaces any air in the tubing 208 such that the tubing 208 becomes filled with saline.

After priming the tubing 208 with saline, the tubing 208 may be preloaded according to an injection protocol with one or medical fluids associated with a clinical or therapeutic fluid delivery procedure to be performed on the patient. The one or more medical fluids may be drawn into a first of the plurality of syringes 132 during a filling procedure as described above with reference to FIG. 2, and then saline may be delivered to the SUDS 190 and used to prime the tubing 208 as described above with reference to FIGS. 3A-3B. Delivery of the one or more medical fluids to the SUDS 190 during the preloading operation will then partially or entirely displace the saline from the tubing 208 by pushing the saline through the waste outlet port 204 and into the waste reservoir 156. At this point, the tubing 208 may be connected to the patient and the injection protocol may be initiated. Because the tubing 208 is, at this stage, partially or entirely filled with the one or more medical fluids rather than saline, needless injection of saline into the patient as part of the fluid delivery procedure may be avoided. In some examples, a catheter, vascular access device, needle, or additional fluid path set to facilitate fluid delivery to the patient may be connected to the tubing 208 prior to preloading of the tubing 208 such that the one or more medical fluids are also preloaded into the vascular access device, needle, or additional fluid path set.

Figure 7A:
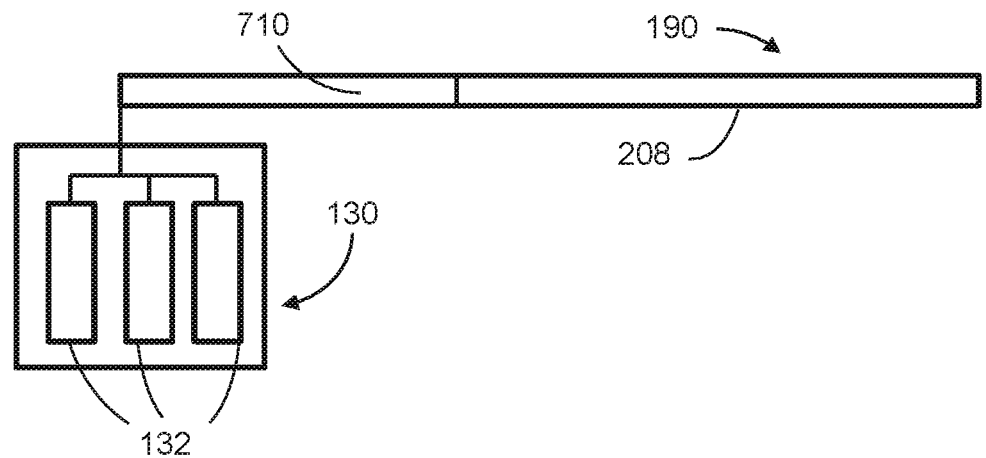
FIG. 7A is a schematic diagram of a partially preloaded single-use disposable set connector in accordance with one example.
Figure 7B:
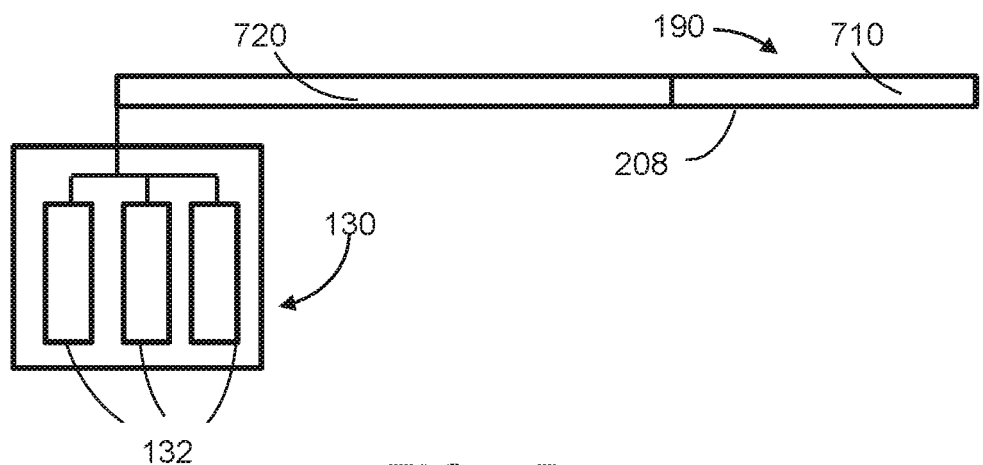
FIG. 7B is a schematic diagram of a fully preloaded single-use disposable set connector in accordance with the example of FIG. 7A.

An exemplary method of preloading the SUDS 190 for performing an injection protocol will now be described with reference to FIGS. 7A-7B. In the presently described exemplary case, the tubing 208 of the SUDS 190 has an internal volume of 8 milliliters. The injection protocol, in this exemplary case an MR injection, calls for delivery of 5 milliliters of contrast solution followed by delivery of 20 milliliters of flushing agent. Prior to the preloading, the contrast solution may be drawn into a first of the plurality of syringes 132 from a first of the bulk fluid sources 120, and the flushing agent may be drawn into a second of the plurality of syringes 132 from a second of the bulk fluid sources 120. The valves 136 of the MUDS 130 may then be closed such that subsequent actuation of the syringes 132 will direct the fluid contained therein to the SUDS 190, as described above. During preloading, the first of the syringes 132 is actuated to advance a first bolus 710 of 5 milliliters of contrast solution into a proximal end of the tubing 208, as shown in FIG. 7A. If a priming operation was performed prior to preloading, advancement of the first bolus 710 in the tubing 208 displaces an equal volume of residual fluid from the priming operation and ejects that residual fluid from the distal end of the tubing 208. The second of the syringes 132 is then actuated to advance a second bolus 720 of the flushing agent into a proximal end of the tubing 208, as shown in FIG. 7B. Advancement of the second bolus 720 consequently pushes the first bolus 710 toward the distal end of the tubing 208 and ejects further residual fluid from the priming operation, if present, from the tubing 208. In this example, because the total volume of contrast solution (5 milliliters) and flushing agent (20 milliliters) for the injection protocol exceeds the capacity of the tubing 208 (8 milliliters), the initial volume of the second bolus 720 is substantially equal to capacity of the tubing 208 (8 milliliters) minus the volume of the first bolus 710 (5 milliliters). Thus, the initial volume of the second bolus 720 is 3 milliliters. Once the second bolus 720 is advanced into the tubing 208, the preloading is complete, and actuation of the second of the syringes 132 is halted.

At this stage, the first bolus 710 occupies the tubing 208 immediately adjacent the distal end of the tubing 208, and the second bolus 720 occupies the tubing 208 adjacent the first bolus 710 and the proximal end of the tubing 208, as may be appreciated from FIG. 7B. No residual fluid from the flushing/priming operation, or a negligible amount thereof, is present in the tubing 208. The distal end of the tubing 208 may then be connected to the patient, and the injection protocol may be initiated. The second of the syringes 132 is again actuated to advance the remaining volume of flushing agent called for in the injection protocol into the tubing 208. That is, an additional 17 milliliters of flushing agent is injected into the patient, equal to the total volume (20 milliliters) called for in the injection protocol minus the initial volume (3 milliliters) of the second bolus 720. As the remaining volume of flushing agent called for in the injection protocol is advanced into the tubing 208, the first bolus 710 and the second bolus 720 are subsequently displaced from the tubing 208 and injected into the patient. The injection protocol is then complete. In this exemplary case, the patient receives a total injection volume of 25 milliliters of fluid, equal to the preloaded volume of 8 milliliters (i.e., 5 milliliters of the first bolus 710 plus 3 milliliters of the second bolus 720), plus the 17-milliliter remaining volume of flushing agent injected after the tubing 208 is connected to the patient. Upon injection of the total volume (25 milliliters), 8 milliliters of the flushing agent will remain in the tubing 208 after the injection protocol is completed.

As is apparent from the above description of the exemplary case shown in FIGS. 7A-7B, preloading the tubing 208 allows the injection protocol to be performed without needlessly injecting residual fluid from the priming operation into the patient. Additionally, the contrast solution is injected into the patient with minimal delay, since the first bolus 710 is immediately adjacent the distal end of the tubing 208, and no flushing/priming fluid must be evacuated from the tubing 208 before the first bolus 710 reaches the patient. Moreover, in distinction from simply priming the tubing 208 with contrast solution, preloading the tubing 208 allows for the first bolus 710 to contain a volume of less than the total capacity of the tubing 208. As such, the patient is not injected with extra contrast solution beyond that called for in the injection protocol.

Figure 8:
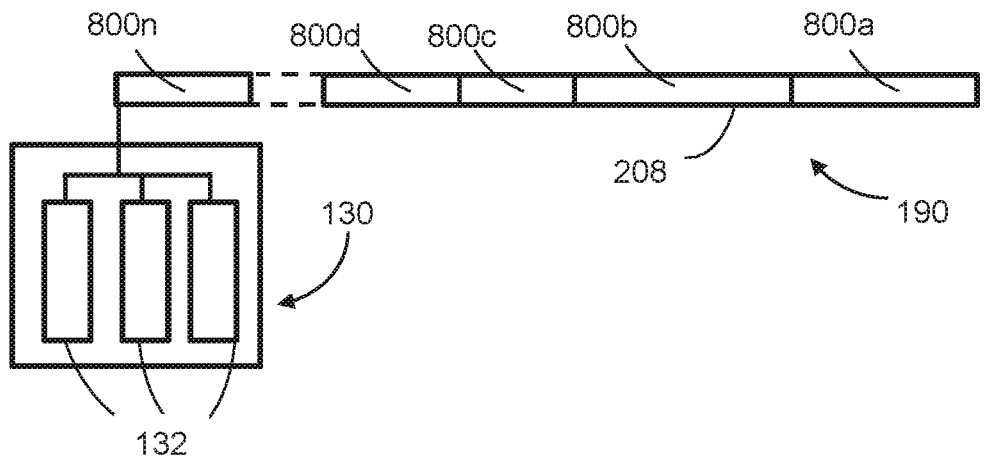
FIG. 8 is a schematic diagram of a fully preloaded single-use disposable set connector in accordance with another example.

Of course, the exemplary case described above with reference to FIGS. 7A-7B is not limiting to the variety of injection protocols that may be accomplished by preloading the SUDS 190. With reference to FIG. 8, a generic case shows that any number or boluses 800a-800n may be preloaded into the tubing 208 in the same manner as described for the first and second boluses 710, 720 of FIGS. 7A-7B. The number of boluses 800a-800n is limited only by the capacity of the tubing 208. Some of the boluses 800a-800n may contain the same fluid. For example, if the injection protocol calls for alternating injections of contrast solution and flushing agent, first and third boluses 800a, 800c may contain contrast solution, while second and fourth boluses 800b, 800d may contain flushing agent. This may be achieved by alternatively actuating and de-actuating the syringes 132 respectively containing the contrast solution and the flushing agent. In some examples, an individual one of the boluses 800a-800n may contain multiple types of fluids in whatever ratio the injection protocol requires. This may be achieved by actuating multiple of the syringes 132 simultaneously. In some examples, the boluses 800a-800n may have different volumes from one another, or the same volumes as one another. In some examples, only a single bolus 800a may be preloaded, resulting in essentially the same effect as priming the tubing 208 with the fluid contained in the single bolus 800a would produce.

With continued reference to FIG. 8 and further reference to FIG. 1, an operator may design and/or initiate a preloading procedure, including the quantities, volumes, and fluid contents of the boluses 800a-800n, utilizing the at least one control button 126 of the fluid injector system 100 and/or the user interface 124. Additionally, the operator may utilize the at least one control button 126 of the fluid injector system 100 and/or the user interface 124 to cancel a preloading procedure. The user interface 124 may include a sensory indicator of preloading status so that the operator is alerted when the preloading is completed and the tubing 208 may be connected to the patient. The sensory indicator may include, for example, a light, icon, status bar, audible sound, or a combination thereof. The sensory indicator may also indicate that, because the tubing 208 is preloaded, there is minimal delay in the contrast solution (or other medical fluid called for by the injection protocol) being delivered to the patient. The operator may thus utilize the sensory indicator to adjust other portions of a therapeutic procedure, such as the timing of an MR or CT scan, to match the timing of contrast solution delivery to the patient.

Now referring again to FIGS. 6 through 8, the operator may enter a command including an injection protocol via the user input interface 928 of the electronic control device 900. The processor 904 of the electronic control device 900 may be programmed or configured to preload the SUDS 190 based on information contained in the injection protocol, such as the number of boluses, the medical fluid of each bolus, and the volume of each bolus. The processor 904 of the electronic control device 900 may be programmed or configured to actuate the syringes 132 in the manner required to achieve the preloading injection protocol. For example, referring to the exemplary case shown in FIGS. 7A-7B, the processor 904 may be programmed or configured to actuate the first of the syringes 132 to advance 5 milliliters of contrast solution into the tubing 208 to form the first bolus 710. The processor 904 may be further programmed or configured to actuate the second of the syringes 132 to advance 3 milliliters of flushing agent into the tubing 208 to form the second bolus 720. In some examples, the processor 904 may be configured to calculate the available capacity of the tubing 208 after the first bolus 710 is advanced to determine the volume of the second bolus 720. In the example of FIGS. 7A-7B, the processor 904 may calculate that after advancing the 5 milliliters of contrast solution called for by the injection protocol, the tubing 208 has 3 milliliters of remaining capacity. The processor 904 may then determine that of the 20 milliliters of flushing agent called for in the injection protocol, only 3 milliliters can be advanced to the tubing 208 without ejecting the first bolus 710. The processor 904 thus advances only 3 milliliters of flushing agent from the second of the syringes 132. The processor 904 then advances the remaining 17 milliliters of flushing agent called for by the injection protocol, plus an additional 8 milliliters of flushing agent to account for the capacity of the tubing 208 after the SUDS 190 has been connected to the patient in order to inject the entirety of the 20 milliliters of flushing agent called for in the injection protocol. More generally, the processor 904 may be programmed or configured to calculate the available capacity of the tubing 208, i.e., the total capacity of the tubing 208 minus the volume of any already advanced boluses 710, 720, 800a-800n, and to size subsequent boluses 710, 720, 800a-800n to have a volume of no more than the available capacity.

Figure 9:
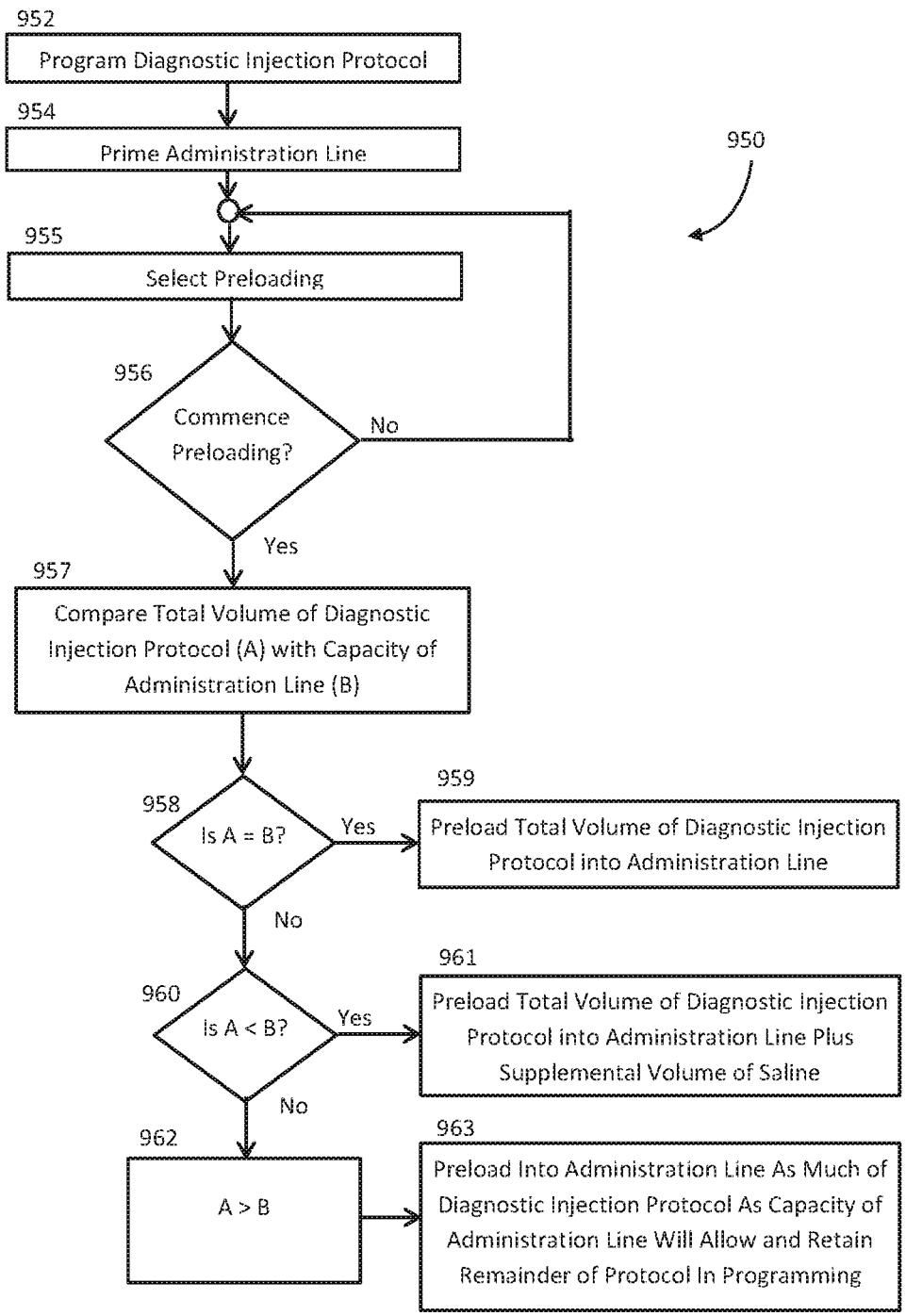
FIG. 9 is a flow chart illustrating a method of showing a preloading operation in accordance with one example.

Referring now to FIG. 9, an example of a method 950 relating to the at least partial preloading of an administration line will now be described with regard to method steps 952-963. The method illustrated in FIG. 9 may be utilized, in some examples, to preload the tubing 208 as described above with respect to FIGS. 7A-8. The method 950, as performed by the fluid injector system 100, may be implemented by a computer program product. The computer program product may include at least one non-transitory computer-readable medium having one or more instructions executable by at least one processor to cause the at least one processor to execute all or part of the diagnostic injection procedure. In some examples or aspects, the at least one non-transitory computer-readable medium and the at least one processor may include or correspond to the memory 908 and processor 904, respectively, as described above with reference to FIG. 6.

Throughout the execution of steps 952-963 of the method 950, the at least one processor 904 may be in operative communication with the user interface 124 to facilitate entry of one or more user inputs associated with control of a plurality of operations of the fluid injector system 100. For example, a set of the one or more user inputs may be associated with control of a corresponding set of the plurality of operations involved with enabling the selection and commencement of the at least partial preloading of the administration line with the first and/or the second fluids in accordance with the one or more phases of the diagnostic injection protocol. The user inputs may include, for example, a "Select Preloading" command, a "Commence Preloading" command, and a "Disable Preloading" command. Each of these user input commands will be discussed in greater detail below in conjunction with the method step associated with each of the user inputs. The user inputs may be entered into the user interface 124 via a user input interface 928, as discussed above with reference to FIG. 6. A variety of input devices of the user input interface 928 may be utilized to receive the user inputs such as, for example, a microphone, a trackball, a joystick, a touchpad, a touch-screen, a scanner, a keyboard, a mouse, and combinations thereof.

With continued reference to FIG. 9, at step 952 the at least one processor 904 of the fluid injector system 100 may be programmed with a diagnostic injection protocol. The diagnostic injection protocol may include one or more phases according to which at one of a first fluid container and a second container may be selectively actuatable by at least one drive component. In some examples, each of the first and second fluid containers may be one or more of the syringes 132, with the first fluid container configured to be filled with a first fluid (e.g. a contrast solution) and the second fluid container configured to be filled with a second fluid (e.g. a flushing agent). The at least one drive component may be, for example, one or more of the piston elements 103. The diagnostic injection protocol, when executed by the at least one processor 904, may cause the at least one drive component to actuate one or more of the fluid containers via piston elements 103 and thereby inject at least one of the first fluid and the second fluid into the patient via the administration line. As noted above, the administration line may be, for example, the tubing 208.

With continued reference to FIG. 9, at step 954 the at least one processor 904 of the fluid injector system 100 may actuate the second fluid container to prime the administration line, as described above. That is, the flushing agent, from the MUDS 130 is injected through the connection port 192 into the tubing 208 of the SUDS 190, and eventually flows to connector 214 at the distal end of SUDS 190. Any excess flushing agent can then drip from connector 214 into the waste reservoir 156 to which connector 214 is typically connected during the priming operation. This purges air from the fluid injector system 100 by forcing air in the MUDS 130 and the SUDS 190 out the distal end 212 of the tubing 208. The flushing agent thus displaces any air in the tubing 208 such that the tubing 208 becomes filled with the flushing agent.

With continued reference to FIG. 9, at step 955 the at least one processor 904 of the fluid injector system 100 may be programmed or configured to enable selection of at least partial preloading of into the administration line. The at least partial preloading may include at least one of the first fluid and second fluid in accordance with the one or more phases of the diagnostic injection protocol. The at least partial preloading may be determined, or selected by, the at least one processor 904 based on the diagnostic injection protocol. In particular, the volume of the first fluid and/or the volume of the second fluid to be preloaded into the administration line may be determined, by the at least one processor 904, based on a volume of the first fluid and/or a volume of the second fluid prescribed in one or more phases of the diagnostic injection protocol. Step 955 may be initiated by the user entering the "Select Preloading" command as a user input into the user interface 124. Once the diagnostic injection protocol has been programmed and the administration line primed, entry of the "Select Preloading" command will cause the at least one processor 904 to ready the fluid injector system 100 for at least partial preloading of the diagnostic injection protocol into the administration line. For example, entry of the "Select Preloading" command will cause the at least one processor 904 to ready the fluid injector system 100 to accept user input of the "Commence Preloading" command at step 956 of the method 950.

With continued reference to FIG. 9, at step 956, the at least one processor 904 determines whether to commence preloading in accordance with the diagnostic injection protocol. In some examples, the at least one processor 904 may await entry of the "Commence Preloading" command from the user into the user interface 124. If the "Commence Preloading" command is received subsequent to the "Select Preloading" command, the at least one processor 904 determines to commence preloading and advances the method to step 957. If the "Commence Preloading" command is not received subsequent to the "Select Preloading" command, or if the user instead enters the "Disable Preloading" command, the at least one processor returns to step 955 and awaits the user to re-enter the "Select Preloading" command.

With continued reference to FIG. 9, at step 957, after determining to commence the preloading operation, the at least one processor 904 compares the total volume of the first fluid and the second fluid to be injected according to the diagnostic injection protocol (A) to the volume capacity of the administration line (B).

At step 958, the at least one processor determines whether the total volume of the first fluid and the second fluid to be injected according to the diagnostic injection protocol (A) is equal to the capacity of the administration line (B). If the at least one processor 904 determines that the total volume of the first fluid and the second fluid to be injected according to the diagnostic injection protocol (A) is equal to the capacity of the administration line (B), the at least one processor 904, at step 959, actuates one or more of the fluid containers and thereby preloads into the administration line the total volume of the diagnostic injection protocol in accordance with the one or more phases thereof. For example, if the administration line has a capacity of 8 milliliters, and the total volume of the first and second fluid prescribed by the diagnostic injection protocol is 8 milliliters, the at least one processor 904 preloads the 8 milliliters of the fluid prescribed by the fluid injection protocol into the administration line. In some examples, actuating one or more of the fluid containers includes actuating the piston elements 103 associated with the syringes 132 to advance at least a portion of the fluid contained within the syringes 132 into the tubing 208. As a consequence of the preloading, the volume of the second fluid used in the priming of the administration line is expelled therefrom. In step 959, because the total volume of the first fluid and the second fluid to be injected according to the diagnostic injection protocol is equal to the capacity of the administration line, the entirety of the fluid required by the diagnostic injection protocol is advanced into the administration line during preloading.

If, at step 958, the at least one processor 904 determines that the total volume of the first fluid and the second fluid to be injected according to the diagnostic injection protocol (A) is not equal the capacity of the administration line (B), the at least one processor 904 then determines, at step 960, whether the total volume of the first fluid and the second fluid to be injected according to the diagnostic injection protocol (A) is less than the capacity of the administration line (B). If the at least one processor 904 determines that the total volume of the first fluid and the second fluid to be injected according to the diagnostic injection protocol (A) is less than the capacity of the administration line (B), the at least one processor 904, at step 961, actuates one or more of the fluid containers and thereby preloads into the administration line the total volume of the diagnostic injection protocol in accordance with the one or more phases thereof. In some examples, the at least one processor 904 then actuates the second fluid container to preload the administration line with a supplemental volume of the second fluid equal to the capacity of the administration line minus the total volume of the diagnostic injection protocol. For example, if the administration line has a capacity of 8 milliliters, and the total volume of the first and second fluid prescribed by the diagnostic injection protocol is 5 milliliters, the at least one processor 904 preloads the 5 milliliters of the fluid prescribed by the fluid injection protocol into the administration line, followed by a supplemental volume of 3 milliliters to bring the total preloaded volume to 8 milliliters, or equal to the capacity of the administration line. This readies the diagnostic injection protocol for immediate injection into the patient. In some examples, actuating one or more of the fluid containers includes actuating the piston elements 103 associated with the syringes 132 to advance at least a portion of the fluid contained within the syringes 132 into the tubing 208. As a consequence of the preloading, the volume of the second fluid used in the priming of the administration line is expelled therefrom. In step 961, because the total volume of the first fluid and the second fluid to be injected according to the diagnostic injection protocol is less than the capacity of the administration line, the entirety of the fluid required by the diagnostic injection protocol is advanced into the administration line during preloading. The supplement volume of the second fluid is preloaded in order to advance the total volume of the diagnostic injection protocol to the distal end of the administration line, and thereby expel the fluid used in priming the administration line.

If, at step 960, the at least one processor 904 determines that the total volume of the first fluid and the second fluid to be injected according to the diagnostic injection protocol (A) is not less than the capacity of the administration line (B), the at least one processor 904 determines that the total volume of the first fluid and the second fluid to be injected according to the diagnostic injection protocol (A) is greater than the capacity of the administration line (B). The at least one processor 904 then, at step 963, actuates one or more of the fluid containers and thereby preloads into the administration line as much of the first and second fluid, in accordance with the one or more phases of the diagnostic injection protocol, as a capacity of the administration line will allow. For example, if the administration line has a capacity of 8 milliliters, and the total volume of the first and second fluid prescribed by the diagnostic injection protocol is 25 milliliters, the at least one processor 904 preloads the first 8 milliliters of the fluid prescribed by the fluid injection protocol into the administration line. As a consequence of the preloading, the volume of the second fluid used in the priming of the administration line is expelled therefrom. In some examples, actuating one or more of the fluid containers includes actuating the piston elements 103 associated with the syringes 132 to advance at least a portion of the fluid contained within the syringes 132 into the tubing 208. After preloading up to the capacity of the administration line, the at least one processor 904 retains within the programming a remaining portion of the diagnostic injection protocol. For example, if 8 milliliters of fluid is preloaded into the administration line out of a total of 25 milliliters prescribed by the diagnostic injection protocol, the programming retains a log of the remaining 17 milliliters not preloaded into the administration line. The at least one processor 904 will then inject the remaining portion of the diagnostic injection protocol when the diagnostic injection protocol is performed on the patient. That is, when the diagnostic injection protocol is performed on the patient, the 8 milliliters of fluid preloaded into the administration line will be injected into the patient first followed by the 17 milliliters that, prior to the diagnostic injection procedure being performed, had been retained within the programming.

For each diagnostic injection protocol programmed into the fluid injector system 100, the method 950 will include only one of steps 959, 961, and 963. In subsequent diagnostic injection procedures, the same step may be carried out or another one of steps 959, 961, and 963 may be performed as part of the method 950, based on the determinations made by the at least one processor 904 at steps 958, 960, and 962. It is to be understood that the order of steps 958, 960, and 962 may be altered without departing from the scope of the present disclosure. For example, the at least one processor 904 may perform step 962 first, and, if it is determined that the total volume of the first fluid and the second fluid to be injected according to the diagnostic injection protocol (A) is not greater than the capacity of the administration line (B), the at least one processor 904 may subsequently perform steps 958 and/or 960.

With continued reference to FIG. 9, after preloading the administration line according to either step 959, 961, or 963, the at least one processor 904 of the fluid injector system 100 may be programmed or configured to perform the diagnostic injection protocol on the patient. In particular, the at least one processor 904 actuates one or more of the fluid containers to inject the total volume of the first and second fluid prescribed by the protocol into the patient. If the total volume of the first and second fluids prescribed by the protocol is fully preloaded into the administration line as in step 959, the at least one processor 904 will actuate the second fluid container to push a flushing agent into the administration line behind the preloaded fluid only when the diagnostic injection procedure is being performed on the patient. If the total volume of the first and second fluids prescribed by the protocol is preloaded into the administration line along with the supplemental volume of saline as in step 961, the at least one processor 904 will similarly actuate the second fluid container to push flushing agent into the line so as to push the total volume of the diagnostic injection protocol into the patient. When a remaining portion of the diagnostic injection protocol is retained by the programming as in step 963, the remaining portion will be injected into the patient immediately after the portion of the protocol that was actually preloaded into the administration line. This is accomplished by actuating the second fluid container via the at least one processor 904 to push additional flushing agent, in a volume equal to the capacity of the administration line, into the administration line and thereby push the entirety of the diagnostic injection protocol into the patient.

Throughout the execution of steps 952-963 of the method 950, the at least one processor 904 may be in operative communication with the user interface 124 to cause the user interface 124 to display information associated with a status of the at least partial preloading into the administration line of at least one of the first fluid and the second fluid in accordance with the one or more phases of the diagnostic injection protocol. The information associated with the status may include, for example, a total volume of the first and/or the second fluid to be injected according to the diagnostic injection protocol, a volume of the first and/or the second fluid which has been injected at any time during performance of the diagnostic injection protocol, a volume of the first and/or the second fluid which remains to be injected at any time during performance of the diagnostic injection protocol, and/or a flow rate at which the first and/or the second fluid is being injected at any time during performance of the diagnostic injection protocol. The at least one processor 904 may further cause the user interface 124 to display information relating to each of the one or more phases of the diagnostic injection protocol, such as a particular volume and/or flow rate of the first and/or the second fluid to be injected during each phase, and a particular volume and/or flow rate of the first and/or the second fluid being injected during the present phase.

While several examples of fluid delivery systems, computer program products, and methods for preloading a single-use disposable set connector are shown in the accompanying drawings and described hereinabove in detail, other examples will be apparent to, and readily made by, those skilled in the art without departing from the scope and spirit of the disclosure. For example, it is to be understood that this disclosure contemplates that, to the extent possible, one or more features of any example can be combined with one or more features of any other example. Accordingly, the foregoing description is intended to be illustrative rather than restrictive.

We claim:
1. A fluid injector system comprising:
a control device operably associated with at least one drive component for use in actuating a plurality of fluid containers, the plurality of fluid containers capable of being placed in fluid communication with a patient through an administration line with a first of the fluid containers capable of being filled with a first fluid comprising a contrast solution and a second of the fluid containers capable of being filled with a second fluid comprising a flushing agent; and
the control device including at least one processor programmed or configured to:
enable programming of a diagnostic injection protocol comprising one or more phases according to which at least one of the first and the second fluid containers are selectively actuatable by the at least one drive component to enable injection of at least one of the first fluid and the second fluid via the administration line into the patient so as to effect enhancement of at least one region of interest thereof over a scan duration of a diagnostic imaging procedure;
prime the administration line with the second fluid;
enable selection and commencement of at least partial preloading into the administration line of a predetermined volume of at least one of the first fluid and the second fluid in accordance with the one or more phases of the diagnostic injection protocol; and
initiate the diagnostic injection protocol to deliver the predetermined volume of at least one of the first fluid and the second fluid and any remaining volume of at least one of the first fluid and the second fluid in accordance with the one or more phases of the diagnostic injection protocol to the patient via the administration line;
wherein the at least one processor is further programmed or configured to calculate a total volume of the at least one of the first fluid and the second fluid to be injected according to the diagnostic injection protocol such that, upon commencement of at least partial preloading, the at least one processor:
upon determining that the total volume of the at least one of the first fluid and the second fluid to be injected according to the diagnostic injection protocol is equal to the capacity of the administration line, preloads into the administration line the total volume of the diagnostic injection protocol in accordance with the one or more phases thereof and thereby expels from the administration line a volume of the second fluid used in the priming of the administration line therewith;
upon determining that the total volume of the at least one of the first fluid and the second fluid to be injected according to the diagnostic injection protocol is less than the capacity of the administration line, preloads into the administration line the total volume of the diagnostic injection protocol in accordance with the one or more phases thereof followed by a supplemental volume of the second fluid equal to the capacity of the administration line minus the total volume of the diagnostic injection protocol and thereby expels from the administration line the volume of the second fluid used in the priming of the administration line therewith; and upon determining that the total volume of the at least one of the first fluid and the second fluid to be injected according to the diagnostic injection protocol is greater than the capacity of the administration line, preloads into the administration line as much of the at least one of the first fluid and the second fluid in accordance with the one or more phases of the diagnostic injection protocol as a capacity of the administration line will allow and retains within the programming a remaining portion of the diagnostic injection protocol until the diagnostic injection protocol is performed on the patient and thereby expels from the administration line the volume of the second fluid used in the priming of the administration line therewith.

2. The fluid injector system of claim 1, further including a user interface operably associated with the at least one processor, the user interface being configured to accept a plurality of user inputs associated with control of a plurality of operations of the fluid injector system, wherein a set of the plurality of user inputs is associated with the control of a corresponding set of the plurality of operations involved with the enabling of the selection and the commencement of the at least partial preloading into the administration line of the at least one of the first fluid and the second fluid in accordance with the one or more phases of the diagnostic injection protocol.

3. The fluid injector system of claim 2, wherein the set of the plurality of user inputs includes:
   a select preloading command upon entry of which into the user interface the control device readies the fluid injector system for the at least partial preloading of the diagnostic injection protocol into the administration line;
   a commence preloading command upon entry of which into the user interface after the select preloading command the control device actuates the plurality of fluid containers and thereby commences the at least partial preloading into the administration line of at least one of the first fluid and the second fluid in accordance with the one or more phases of the diagnostic injection protocol; and
   a disable preloading command upon entry of which into the user interface after the select preloading command the control device disables an effect of the select preloading command.

4. The fluid injector system of claim 2, wherein the user interface is configured to display information associated with a status of the at least partial preloading into the administration line of at least one of the first fluid and the second fluid in accordance with the one or more phases of the diagnostic injection protocol.

5. The fluid injector system of claim 2, wherein the user interface is configured to display at least one of:
   the total volume of the at least one of the first fluid and the second fluid to be injected according to the diagnostic injection protocol; and
   for each of the one or more phases of the diagnostic injection protocol, a particular volume of the at least one of the first fluid and the second fluid therein and a flow rate at which the particular volume is to be injected into the patient during administration thereof.

6. The fluid injector system of claim 1, wherein the first of the fluid containers comprises a syringe and the second of the fluid containers comprises a syringe.

7. A computer program product for enabling at least partial preloading into an administration line of at least one of a first fluid and a second fluid in accordance with a one or more phases of a diagnostic injection protocol, the computer program product comprising at least one non-transitory computer-readable medium comprising one or more instructions that, when executed by at least one processor, cause the at least one processor to:
   enable programming of the diagnostic injection protocol into a control device of a fluid injector system, the control device operably associated with at least one drive component for use in selectively actuating a plurality of fluid containers, the plurality of fluid containers configured for being placed in fluid communication with a patient through the administration line with a first of the fluid containers capable of being filled with the first fluid comprising a contrast solution and a second of the fluid containers capable of being filled with the second fluid comprising a flushing agent;
   prime the administration line with the second fluid;
   enable selection and commencement of at least partial preloading into the administration line of a predetermined volume of at least one of the first fluid and the second fluid in accordance with the one or more phases of the diagnostic injection protocol; and
   initiate the diagnostic injection protocol to deliver the predetermined volume of at least one of the first fluid and the second fluid and any remaining volume of at least one of the first fluid and the second fluid in accordance with the one or more phases of the diagnostic injection protocol to the patient via the administration line;
   wherein the at least one processor is further programmed or configured to calculate a total volume of the at least one of the first fluid and the second fluid to be injected according to the diagnostic injection protocol such that, upon commencement of at least partial preloading, the at least one processor:
   upon determining that the total volume of the at least one of the first fluid and the second fluid to be injected according to the diagnostic injection protocol is equal to the capacity of the administration line, preloads into the administration line the total volume of the diagnostic injection protocol in accordance with the one or more phases thereof and thereby expels from the administration line a volume of the second fluid used in the priming of the administration line therewith;
   upon determining that the total volume of the at least one of the first fluid and the second fluid to be injected according to the diagnostic injection protocol is less than the capacity of the administration line, preloads into the administration line the total volume of the diagnostic injection protocol in accordance with the one or more phases thereof followed by a supplemental volume of the second fluid equal to the capacity of the administration line minus the total volume of the diagnostic injection protocol and thereby expels from the administration line the volume of the second fluid used in the priming of the administration line therewith; and
   upon determining that the total volume of the at least one of the first fluid and the second fluid to be injected according to the diagnostic injection protocol is greater than the capacity of the administration line, preloads into the administration line as much of the at least one of the first fluid and the second fluid in accordance with the one or more phases of the diagnostic injection protocol as a capacity of the administration line will allow and retains within the programming a remaining portion of the diagnostic injection protocol until the diagnostic injection protocol is performed on the patient and thereby expels from the administration line the volume of the second fluid used in the priming of the administration line therewith.

8. The computer program product of claim 7, wherein the one or more instructions, when executed by at least one processor, further cause the at least one processor to:
receive, from a user interface operably associated with the at least one processor, at least one of a plurality of user inputs associated with control of a plurality of operations of the fluid injector system,
wherein a set of the plurality of user inputs is associated with the control of a corresponding set of the plurality of operations involved with the enabling of the selection and the commencement of the at least partial preloading into the administration line of the at least one of the first fluid and the second fluid in accordance with the one or more phases of the diagnostic injection protocol.

9. The computer program product of claim 8, wherein the set of the plurality of user inputs includes:
a select preloading command upon entry of which into the user interface the control device readies the fluid injector system for the at least partial preloading of the diagnostic injection protocol into the administration line;
a commence preloading command upon entry of which into the user interface after the select preloading command the control device actuates the plurality of fluid containers and thereby commences the at least partial preloading into the administration line of at least one of the first fluid and the second fluid in accordance with the one or more phases of the diagnostic injection protocol; and
a disable preloading command upon entry of which into the user interface after the select preloading command the control device disables an effect of the select preloading command.

10. The computer program product of claim 8, wherein the one or more instructions, when executed by at least one processor, further cause the at least one processor to:
display, via the user interface, information associated with a status of the at least partial preloading into the administration line of at least one of the first fluid and the second fluid in accordance with the one or more phases of the diagnostic injection protocol.

11. The computer program product of claim 8, wherein the one or more instructions, when executed by at least one processor, further cause the at least one processor to:
display, via the user interface, at least one of:
the total volume of the at least one of the first fluid and the second fluid to be injected according to the diagnostic injection protocol; and
for each of the one or more phases of the diagnostic injection protocol, a particular volume of the at least one of the first fluid and the second fluid therein and a flow rate at which the particular volume is to be injected into the patient during administration thereof.

12. The computer program product of claim 7, wherein the first of the fluid containers comprises a syringe and the second of the fluid containers comprises a syringe.

13. A computer-implemented method for enabling at least partial preloading into an administration line of at least one of a first fluid and a second fluid in accordance with a one or more phases of a diagnostic injection protocol, the method comprising:
programming, via at least one processor, the diagnostic injection protocol into a control device of a fluid injector system, the control device operably associated with at least one drive component for use in selectively actuating a plurality of fluid containers, the plurality of fluid containers configured for being placed in fluid communication with a patient through an administration line with a first of the fluid containers capable of being filled with the first fluid comprising a contrast solution and a second of the fluid containers capable of being filled with the second fluid comprising a flushing agent;
priming the administration line with the second fluid;
enabling, via the at least one processor, selection and commencement of at least partial preloading into the administration line of a predetermined volume of at least one of the first fluid and the second fluid in accordance with the one or more phases of the diagnostic injection protocol; and
initiating the diagnostic injection protocol to deliver the predetermined volume of at least one of the first fluid and the second fluid and any remaining volume of at least one of the first fluid and the second fluid in accordance with the one or more phases of the diagnostic injection protocol to the patient via the administration line;
wherein the at least one processor is further programmed or configured to calculate a total volume of the at least one of the first fluid and the second fluid to be injected according to the diagnostic injection protocol such that, upon commencement of at least partial preloading, the at least one processor:
upon determining that the total volume of the at least one of the first fluid and the second fluid to be injected according to the diagnostic injection protocol is equal to the capacity of the administration line, preloads into the administration line the total volume of the diagnostic injection protocol in accordance with the one or more phases thereof and thereby expels from the administration line a volume of the second fluid used in the priming of the administration line therewith;
upon determining that the total volume of the at least one of the first fluid and the second fluid to be injected according to the diagnostic injection protocol is less than the capacity of the administration line, preloads into the administration line the total volume of the diagnostic injection protocol in accordance with the one or more phases thereof followed by a supplemental volume of the second fluid equal to the capacity of the administration line minus the total volume of the diagnostic injection protocol and thereby expels from the administration line the volume of the second fluid used in the priming of the administration line therewith; and
upon determining that the total volume of the at least one of the first fluid and the second fluid to be injected according to the diagnostic injection protocol is greater than the capacity of the administration line, preloads into the administration line as much of the at least one of the first fluid and the second fluid in accordance with the one or more phases of the diagnostic injection protocol as a capacity of the administration line will allow and retains within the programming a remaining portion of the diagnostic injection protocol until the diagnostic injection protocol is performed on the patient and thereby expels from the administration line the volume of the second fluid used in the priming of the administration line therewith.

14. The computer-implemented method of claim 13, further comprising: receiving, from a user interface operably associated with the at least one processor, at least one of a plurality of user inputs associated with control of a plurality of operations of the fluid injector system,
wherein a set of the plurality of user inputs is associated with the control of a corresponding set of the plurality of operations involved with the enabling of the selection and the commencement of the at least partial preloading into the administration line of the at least one of the first fluid and the second fluid in accordance with the one or more phases of the diagnostic injection protocol.

15. The computer-implemented method of claim 14, wherein the set of the plurality of user inputs includes:
a select preloading command upon entry of which into the user interface the control device readies the fluid injector system for the at least partial preloading of the diagnostic injection protocol into the administration line;
a commence preloading command upon entry of which into the user interface after the select preloading command the control device actuates the plurality of fluid containers and thereby commences the at least partial preloading into the administration line of at least one of the first fluid and the second fluid in accordance with the one or more phases of the diagnostic injection protocol; and
a disable preloading command upon entry of which into the user interface after the select preloading command the control device disables an effect of the select preloading command.

16. The computer-implemented method of claim 14, further comprising: displaying, with the user interface, information associated with a status of the at least partial preloading into the administration line of at least one of the first fluid and the second fluid in accordance with the one or more phases of the diagnostic injection protocol.

17. The computer-implemented method of claim 14, further comprising: displaying, with the user interface, at least one of:
the total volume of the at least one of the first fluid and the second fluid to be injected according to the diagnostic injection protocol; and
for each of the one or more phases of the diagnostic injection protocol, a particular volume of the at least one of the first fluid and the second fluid therein and a flow rate at which the particular volume is to be injected into the patient during administration thereof.

18. The computer-implemented method of claim 13, wherein the first of the fluid containers comprises a syringe and the second of the fluid containers comprises a syringe.

* * * * *

UNITED STATES PATENT AND TRADEMARK OFFICE
CERTIFICATE OF CORRECTION

PATENT NO. : 12,171,979 B2  
APPLICATION NO. : 17/043802  
DATED : December 24, 2024  
INVENTOR(S) : Volkar et al.

Page 1 of 1

It is certified that error appears in the above-identified patent and that said Letters Patent is hereby corrected as shown below:

In the Specification

In Column 2, Line 2, delete "Mill" and insert -- MRI --, therefor.

In Column 25, Line 66, delete "or" and insert -- of --, therefor.

In the Claims

In Column 34, Line 3, in Claim 7, delete "a one" and insert -- one --, therefor.

In Column 36, Line 1, in Claim 13, delete "a one" and insert -- one --, therefor.

Signed and Sealed this  
Eighteenth Day of February, 2025

Coke Morgan Stewart  
*Acting Director of the United States Patent and Trademark Office*